(12) United States Patent
Andjelic et al.

(10) Patent No.: US 10,086,109 B2
(45) Date of Patent: Oct. 2, 2018

(54) ABSORBABLE MEDICAL DEVICES BASED ON NOVEL FILMS AND FOAMS MADE FROM SEMI-CRYSTALLINE, SEGMENTED COPOLYMERS OF LACTIDE AND EPSILON-CAPROLACTONE EXHIBITING LONG TERM ABSORPTION CHARACTERISTICS

(71) Applicant: Ethicon, Inc., Somerville, NJ (US)

(72) Inventors: Sasa Andjelic, Nanuet, NY (US); Dennis D. Jamiolkowski, Long Valley, NJ (US); Jackie Donners, Pennington, NJ (US); Mark Timmer, Jersey City, NJ (US)

(73) Assignee: Ethicon, Inc., Somerville, NJ (US)

( * ) Notice: Subject to any disclaimer, the term of this patent is extended or adjusted under 35 U.S.C. 154(b) by 183 days.

(21) Appl. No.: 14/728,177

(22) Filed: Jun. 2, 2015

(65) Prior Publication Data
US 2016/0354510 A1      Dec. 8, 2016

(51) Int. Cl.
| | | |
|---|---|---|
| *A61L 24/04* | (2006.01) | |
| *C08J 5/18* | (2006.01) | |
| *C08L 67/04* | (2006.01) | |
| *A61L 24/00* | (2006.01) | |
| *C08G 63/08* | (2006.01) | |
| *C08J 9/04* | (2006.01) | |
| *C08J 9/26* | (2006.01) | |
| *A61L 27/18* | (2006.01) | |
| *A61L 27/56* | (2006.01) | |
| *A61L 27/58* | (2006.01) | |

(Continued)

(52) U.S. Cl.
CPC ............ *A61L 24/046* (2013.01); *A61L 24/001* (2013.01); *A61L 24/0036* (2013.01); *A61L 27/18* (2013.01); *A61L 27/56* (2013.01); *A61L 27/58* (2013.01); *A61L 31/06* (2013.01); *A61L 31/146* (2013.01); *A61L 31/148* (2013.01); *C08G 63/08* (2013.01); *C08J 5/18* (2013.01); *C08J 9/04* (2013.01); *C08J 9/26* (2013.01); *C08L 67/04* (2013.01); *C08G 2101/00* (2013.01); *C08J 2201/03* (2013.01); *C08J 2201/0482* (2013.01); *C08J 2205/02* (2013.01); *C08J 2300/16* (2013.01); *C08J 2367/04* (2013.01)

(58) Field of Classification Search
CPC .. A61L 24/0036; C08J 5/18; C08J 9/04; C08J 9/26; C08J 2300/16; C08J 2367/04
See application file for complete search history.

(56) References Cited

U.S. PATENT DOCUMENTS

| | | |
|---|---|---|
| 4,664,859 A | 5/1987 | Knoop |
| 4,769,279 A | 9/1988 | Graham |

(Continued)

OTHER PUBLICATIONS

Harwood, H. James, "The Characterization of Sequence Distribution in Copolymers", Polymer Letters, vol. 2, (1964), pp. 601-607.

(Continued)

*Primary Examiner* — Hai Vo
(74) *Attorney, Agent, or Firm* — E. Richard Skula

(57) ABSTRACT

Absorbable medical devices based on novel foams and films made from semi-crystalline, segmented copolymers of lactide and epsilon-caprolactone exhibiting long term absorption characteristics are disclosed. Also disclosed are methods of producing said foams and films, and useful polymer solutions.

4 Claims, 9 Drawing Sheets

Foams from Example 7 (10% w/w concentration)
[Lac/Cap 64/36]

Day 64

(51) Int. Cl.
*A61L 31/06* (2006.01)
*A61L 31/14* (2006.01)
*C08G 101/00* (2006.01)

(56) References Cited

U.S. PATENT DOCUMENTS

| | | | |
|---|---|---|---|
| 4,942,087 | A | 7/1990 | Motook et al. |
| 5,133,739 | A | 7/1992 | Bezwada et al. |
| 5,468,253 | A | 11/1995 | Bezwada et al. |
| 5,510,176 | A | 4/1996 | Nakamura et al. |
| 6,355,699 | B1 | 3/2002 | Vyakarnam et al. |
| 6,712,838 | B2 | 3/2004 | D'Aversa et al. |
| 7,332,050 | B2 | 2/2008 | Kim |
| 7,934,917 | B2 | 5/2011 | Chu et al. |
| 7,943,683 | B2 | 5/2011 | Rizk et al. |
| 8,030,434 | B2 | 10/2011 | Ikeda et al. |
| 8,236,904 | B2 | 8/2012 | Andjelic et al. |
| 8,278,409 | B2 | 10/2012 | Erneta et al. |
| 8,636,942 | B2 | 1/2014 | Komura et al. |
| 2013/0005829 | A1* | 1/2013 | Jamiolkowski ......... A61L 31/06 514/717 |
| 2013/0236499 | A1 | 9/2013 | Andjelic |

OTHER PUBLICATIONS

Karimi, M. et al. "Formation and Size Distribution of Pores in poly (e-caprolactone)Foams Prepared by Pressue Quenching Using Supercritical $CO_2$", J. of Supercritical fluids, 61, (2012) pp. 175-190.

Baimark, Y. et al. "Synthesis, Characterization and Melt Spinning of a block copolymer of L-lactide and e-caprolactone for Potential Use as an Absorbable Monofilament Surgical Suture", J. of Materials Science: Materials in Medicine, 16, (2005, pp. 699-707.

Barry, John J. et al. "Supercritical Cabon Dioxide: Putting the Fizz into Biomaterials", Phil. Trans. R. Soc. (2006), 364, pp. 249-261.

Vanhoorne, P. et al. Macromolecular Engineering of Polylactones and Polylactides. 7. Structual Analysis of Copolyesters of e-Caprolactone and L-or D,L-Lactide Initiated by Al $(O^iPr)_3$.

Wei, Z. et al. "Microstructure Analysis and Thermal Properties of L-lactide/e-caprolactone Copolymers Obtained with Magnesium Octoate", Polymer, 50, (2009), pp. 1423-1429.

* cited by examiner

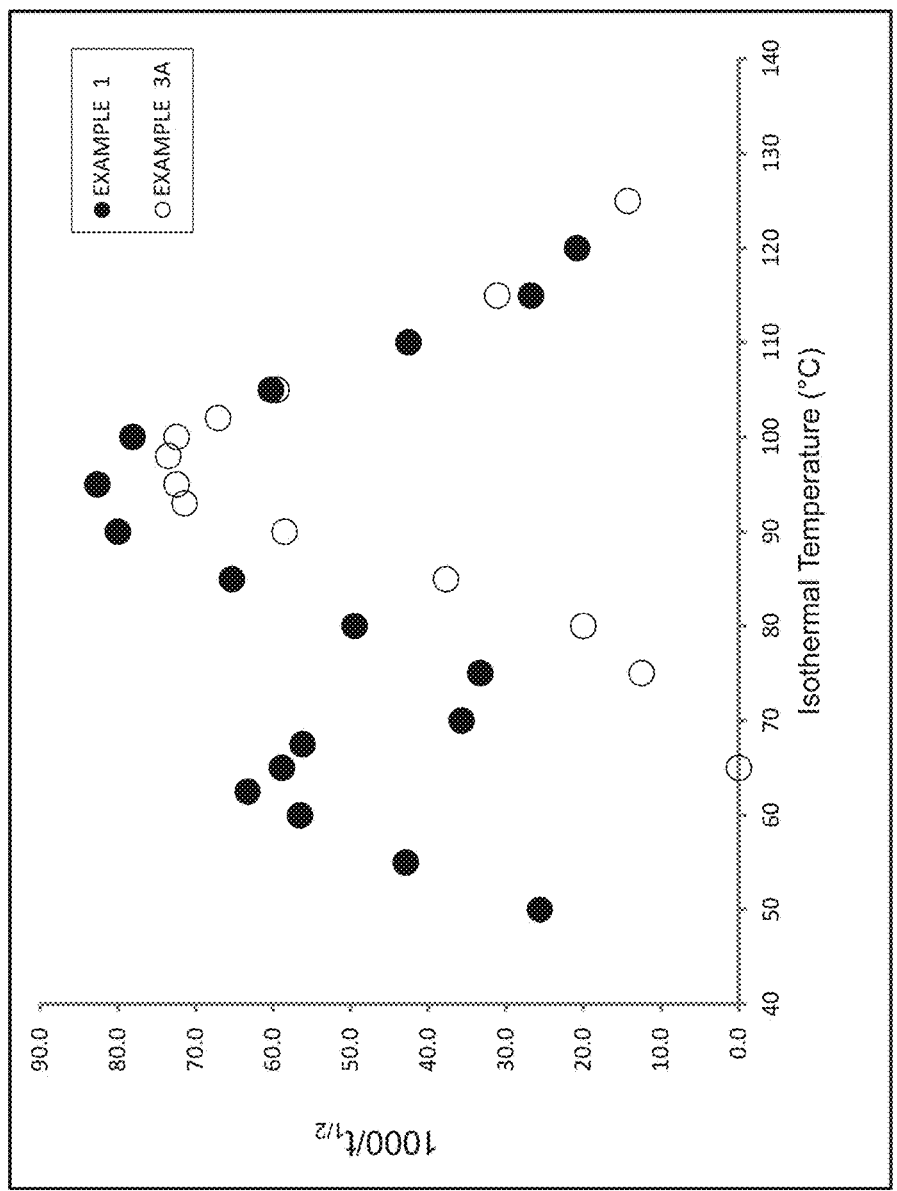
Figure 1. Isothermal Crystallization Kinetics, as Measured by DSC, of the Two Inventive Copolymers

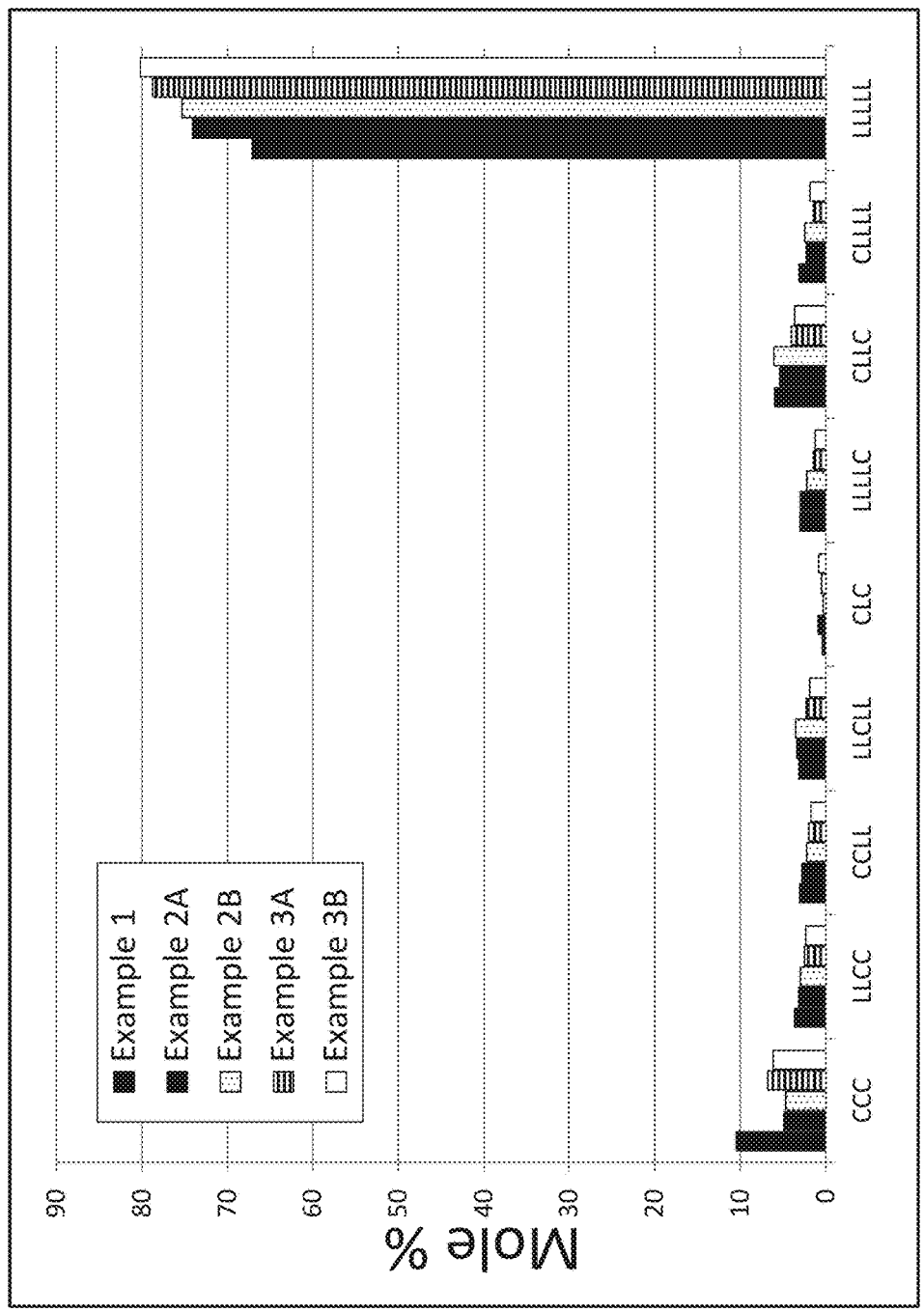
Figure 2. ¹³C NMR Sequence Length for Inventive Resins

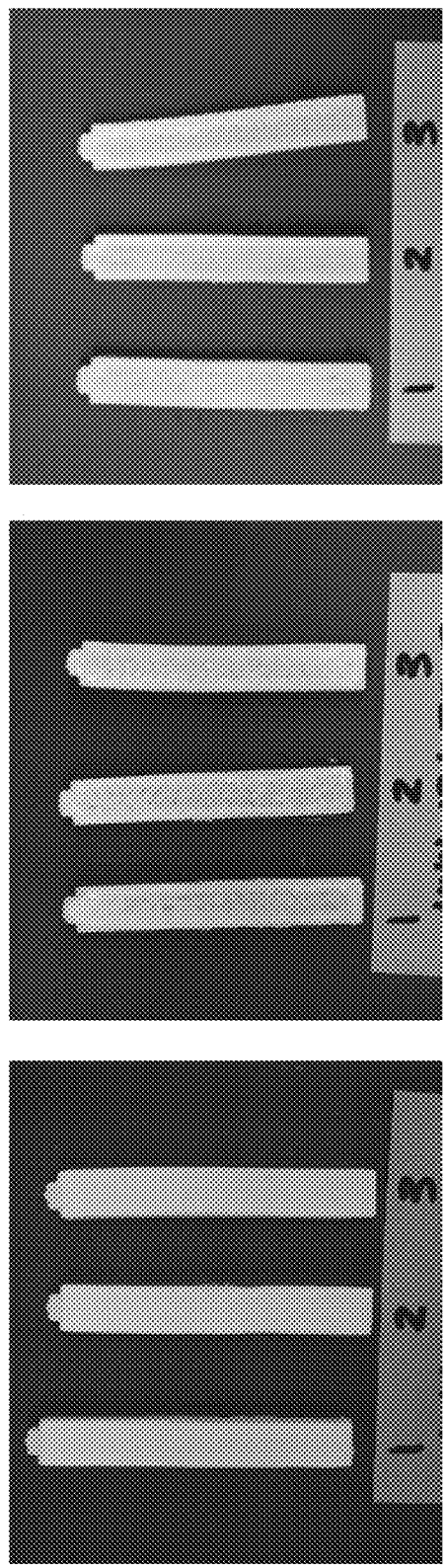
FIG. 3A: Day 0    FIG. 3B: Day 28    FIG. 3C: Day 64
Foams from Example 7 (10% w/w concentration) [Lac/Cap 64/36]

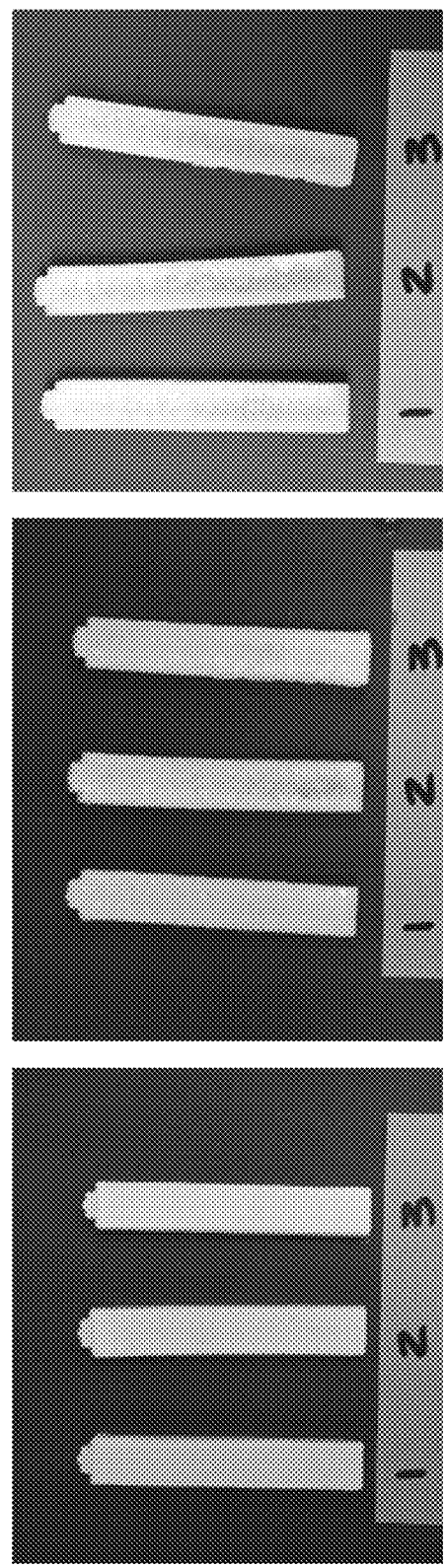
FIG. 4A: Day 0
FIG. 4B: Day 28
FIG. 4C: Day 64
Foams from Example 8 (10% w/w concentration) [Lac/Cap 72/28]

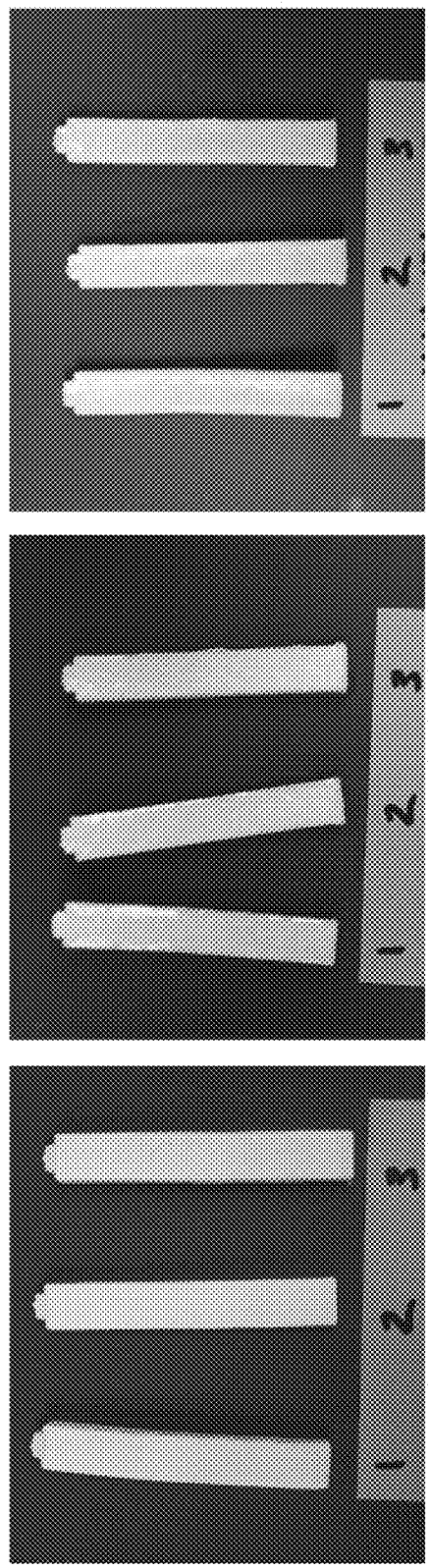
FIG. 5A: Day 0    FIG. 5B: Day 28    FIG. 5C: Day 64

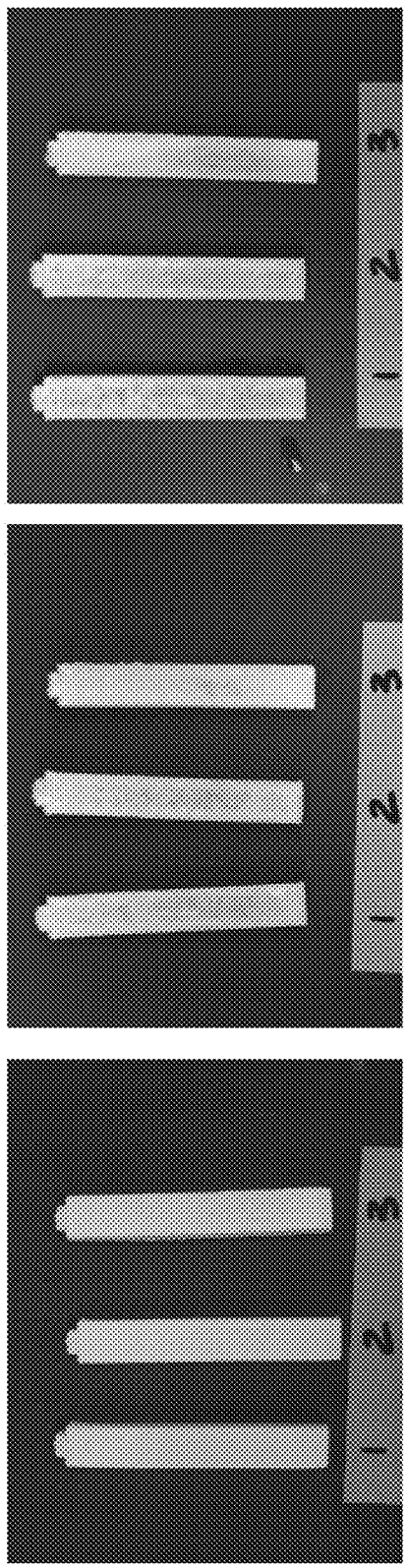
FIG. 6A: Day 0   FIG. 6B: Day 28   FIG. 6C: Day 64

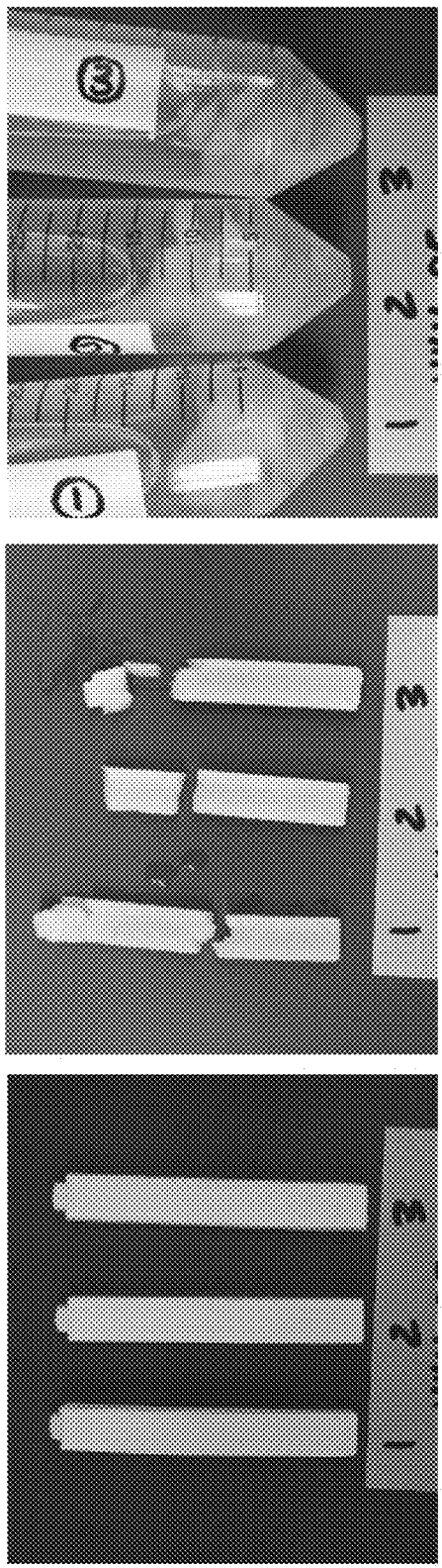
FIG. 7A: Day 0  FIG. 7B: Day 28  FIG. 7C: Day 64

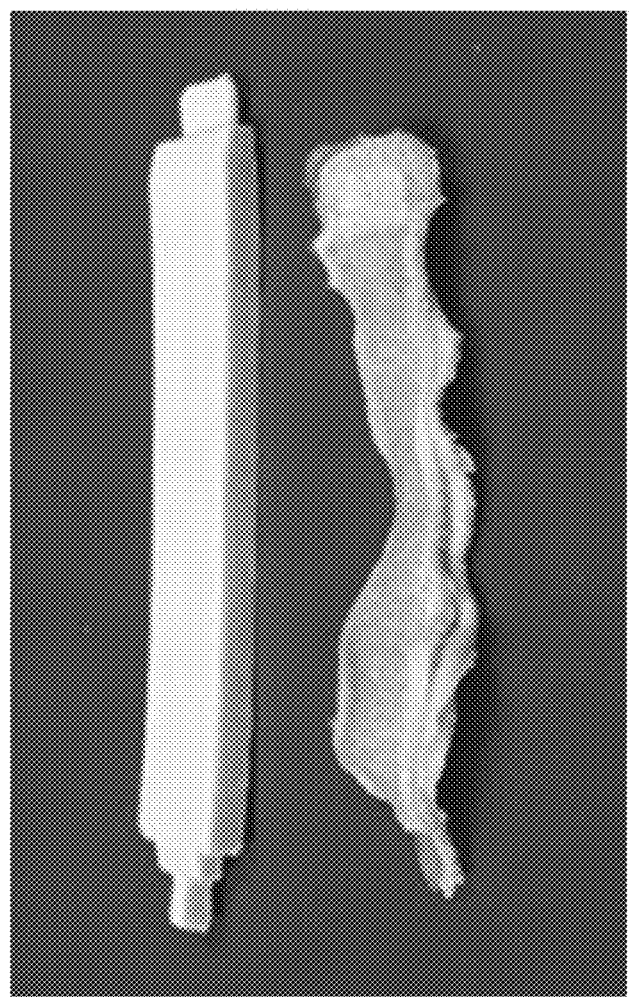
FIG. 8: Foams from 36/64 Caprolactone and Glycolide with Endblocks Comparator (10% w/w concentration)

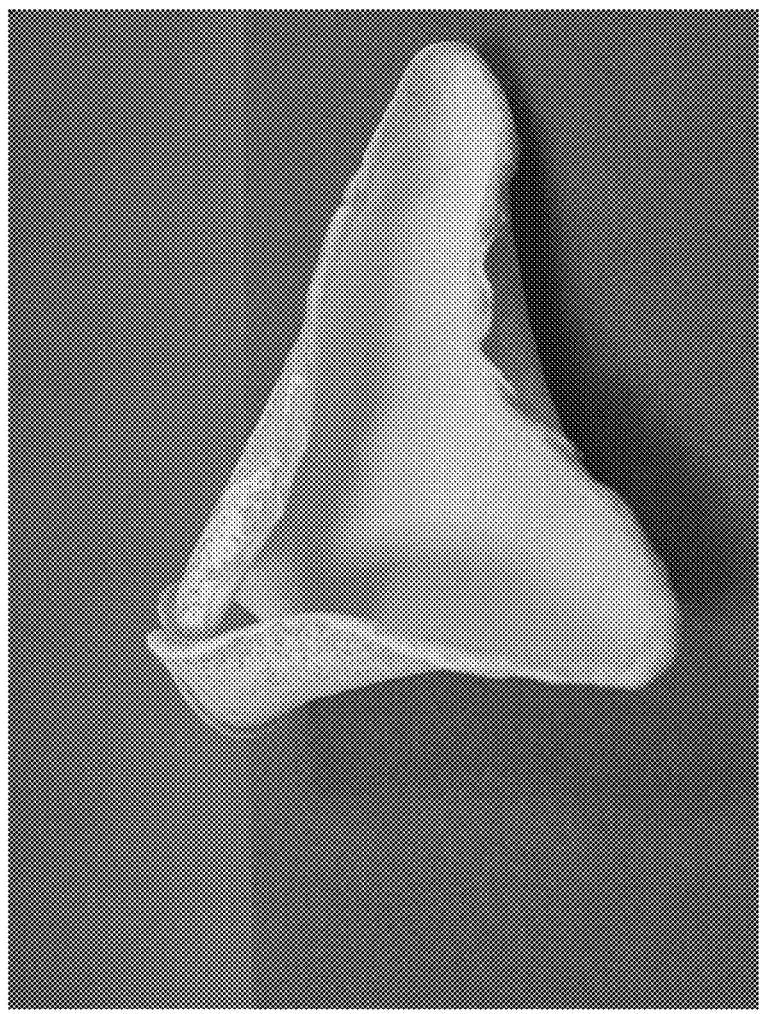
FIG. 9: Foams from 36/64 Caprolactone and Glycolide with Endblocks Comparator (10% w/w concentration)

ABSORBABLE MEDICAL DEVICES BASED ON NOVEL FILMS AND FOAMS MADE FROM SEMI-CRYSTALLINE, SEGMENTED COPOLYMERS OF LACTIDE AND EPSILON-CAPROLACTONE EXHIBITING LONG TERM ABSORPTION CHARACTERISTICS

FIELD OF THE INVENTION

This invention relates to novel semi-crystalline, block copolymers of lactide and epsilon-caprolactone for long term absorbable medical applications, in particular, medical devices such as surgical foams and films.

BACKGROUND OF THE INVENTION

Synthetic absorbable polyesters are well known in the art. The terms absorbable, bioabsorbable, bioresorbable, resorbable, biodegradable are used herein interchangeably. The open and patent literature particularly describe polymers and copolymers made from glycolide, L(−)-lactide, D(+)-lactide, meso-lactide, epsilon-caprolactone, p-dioxanone, and trimethylene carbonate.

A very important aspect of any absorbable medical device is the length of time that its mechanical properties are retained in vivo. For example, in some surgical applications it is important for the device to retain strength for a considerable length of time in order to allow the body the time necessary to heal while performing its desired function. Such slow healing situations include, for example, diabetic patients or bodily areas having poor or diminished blood supply. Absorbable long term sutures are known and have been made from conventional polymers, primarily from lactide. Examples include a braided suture made from a high-lactide, lactide/glycolide copolymer. Those skilled in the art will appreciate that monofilament and multifilament absorbable sutures exist in the art and that short term and long term absorbable sutures also exist in the art. Long term functioning may be described as retaining a certain amount of mechanical integrity in vivo beyond 10 to 12 weeks post-implantation.

Medical devices in the form of polymeric foams or films are known in the art. What does not presently exist is an absorbable polymer that can be made into a foam that is soft enough to exhibit mechanical elasticity to provide both spring-back when compressed and superior handling characteristics to the surgeon, yet maintain its mechanical properties post-implantation to function effectively long term while fully absorbing. There then remains the problem of providing such a polymer that can meet these needs. There is also a need for an absorbable surgical foam made from such a polymer. Absorbable foams generally come in two basic forms, open cell structures and closed cell structures. Open cell foams are particularly advantageous for tissue engineering applications requiring cell ingrowth. Buttress designs of various sorts have been described for use with mechanical surgical staplers, but an implantable absorbable foam buttress has yet to be provided that meets long term needs.

Foam formation from polymeric materials has been described by various researchers over the years. For instance, foams have been made by melt processes such as extrusion with blowing agents and utilizing supercritical carbon dioxide.

For example, the use of supercritical carbon dioxide in making foams is disclosed in "Formation and size distribution of pores in poly(ε-caprolactone) foams prepared by pressure quenching using supercritical $CO_2$", Karimi, et. al, J. of Supercritical Fluids 61 (2012) 175-190. The use of supercritical carbon dioxide in making foams is also disclosed in "Supercritical Carbon Dioxide: Putting the Fizz into Biomaterials", Barry, et. al, Phil. Trans. R. Soc. A 2006 364, 249-261.

Lyophilization is well known in the art and has been used to prepare foams from synthetic absorbable materials. This process is not without difficulties, however. The polymer to be lyophilized must be soluble in the selected solvent, and there are only a limited number of solvents that are suitable for the lyophilization process. The freezing point of a successful solvent needs to be above that of a reasonable shelf and condenser temperature (~−70° C.), and low enough to conveniently dissolve the resin to be lyophilized. Moreover, the vapor pressure at low temperature needs to be high enough so that the solvent can be sublimated from the frozen state at a reasonable enough rate. Typical solvents conventionally used in lyophilization processes include water, 1,4-dioxane, DMSO, DMF, and certain alcohols. Most absorbable polyesters are hydrophobic in nature while the solvents suitable for lyophilization tend to be polar in nature; this creates solubility issues as it is the rare absorbable polymer that can be dissolved in an appropriate lyophilizing solvent.

The final architecture of a polymeric foam made by lyophilization depends on a number of factors, including the polymer concentration in the solvent. Higher mechanical properties often correlate with the bulk density of the foam; high densities then require higher concentrations of the dissolved polymer; for example, 10 weight percent initial solids dissolved in the lyophilizing solvent versus 3 weight percent initial solids. Although a given polymer may be considered soluble in a solvent, it may not be soluble at the high concentrations that may be needed for foam medical devices. Even those absorbable polymers that are soluble in solvents suitable for lyophilization may present another difficulty arising from the phenomena of premature gel formation. Premature gel formation is known to interfere with the making of homogeneous foams, as is required. Premature gelation is particularly challenging in high concentration solutions. It is believed that the gelation phenomena may be due to inter- and intra-chain molecular associations, similar to what might occur during crystallization in solids, although not as strongly. Once gelation takes place in a lyophilizing polymer solution, it is very difficult for polymer chains to possess the mobility they need during the phase separation that must occur as pure solvent (that is solvent without dissolved polymer) crystallizes. Individual chains are "fixed" in place and cannot disentangle to join a solvent/polymer phase of ever increasing polymer concentration.

It has been noted that lyophilizing solutions having higher polymer concentrations may be achieved by lowering the molecular weight of the given polymer, but this has the disadvantage of lowering the mechanical properties of the resultant foam, to unacceptable levels for most surgical applications.

Absorbable polymeric foams to be used in medical applications must typically exhibit dimensional stability, that is, the foams must not deform while undergoing additional, conventional post-processing treatments such as ethylene oxide sterilization, transportation, warehouse storage, and such. This is often a challenge when working with polymers possessing low glass transition temperatures since molecular mobility is enhanced, thereby readily allowing warping, shrinking and other distortions. The crystallization of the polymer constituting the foam is one means of achieving dimensional stability. It should be noted however that a polymer resulting in too high a level of crystallinity in the foam may result in a final article which is too stiff for a given surgical application. For example, the level of "spring back" may be inadequate. Thus, important mechanical properties may be influenced not only by the polymer itself ($T_g$, etc.) but also by the polymer morphology that develops in the final product, again greatly influenced by the polymer and its thermal history. The level of crystallinity in the resin prior to attempted dissolution is also important in low $T_g$ resins. If the crystallinity is too low the resin pellet (or ground resin) may begin to stick to itself during storage or transportation if exposed to even the slightest elevated temperatures, for example 20° C. The once divided, free-flowing polymer granules gradually aggregate into a large brick-like mass. If the crystallinity of the resin is too high, difficulties may be experienced during attempts to dissolve the resin in the selected solvent; that is, the resin may not properly dissolve.

The lyophilization process is demanding in that it is difficult to produce a suitable product in a robust fashion. If the polymer does not readily dissolve, if it tends to gel too quickly, if it cannot maintain dimensional stability during the process (as well as later during EO sterilization or during transportation), or if the solvent cannot be adequately removed, a suitable foam will not result.

Of course being able to make an absorbable polymeric foam with an appropriate architecture does not complete the challenge; one needs to provide a foam with appropriate ester chemistry to achieve an appropriate hydrolysis profile post-implantation. Retention of mechanical properties for a number of long term surgical applications is critical in slow to heal patients or in slow to heal bodily tissue. Finally, the polymer must still be absorbable; that is, slowly hydrolyze to be removed by the body from the surgical site.

The polymer must then possess certain solubility and crystallization characteristics, as well as certain mechanical and hydrolysis properties, if it is to be suitable for fabricating surgical foam products by the lyophilization method.

The use of some absorbable synthetic polyesters for foam formation via lyophilization processes is known and disclosed in the art. Examples include for example, U.S. Pat. No. 5,468,253, Bezwada, et al., "Elastomeric Medical Device", filed on Jan. 21, 1993 and issued on Nov. 21, 1995, which discloses medical devices or components for medical devices formed from bioabsorbable elastomers comprising a random copolymer of from about 30 to about 70 weight percent of: a) ε-caprolactone, trimethylene carbonate, and ether lactone, or a mixture of these, and b) the balance being substantially glycolide, para-dioxanone, or a mixture of these. U.S. Pat. No. 5,468,253 further discloses bioabsorbable foams made from the elastomers.

U.S. Pat. No. 6,355,699, Vyakarnam, et al., "Process for Manufacturing Biomedical Foams" filed on Jun. 30, 1999 and issued on Mar. 12, 2002 discloses an improved lyophilization process for forming biocompatible foam structures.

The ε-caprolactone/glycolide copolyesters described by Vyakarnam et al. are directed towards elastomeric materials (see col 5, lines 32 to 36). Their one-step, one-pot polymerization process method tends to produce polymers that exhibit a random distribution of monomer repeat units, while the compositions of the Vyakarnam et al. polyesters made by a sequential addition method, which can be used to produce clearly non-random sequence distributions, are outside the scope of the present invention. In general, the substantially random copolymers of Bezwada, et at and Vyakarnam et al. are quite soluble in at least one lyophilizing solvent, 1,4-dioxane, and only form the undesired gels after an extended period of time. This last characteristic is valuable from a manufacturing standpoint in that it allows significant leeway in processing times. An undesirable characteristic, however, of the random ε-caprolactone/glycolide copolyesters described by Bezwada et al. is that their copolymers are able achieve only low levels of crystallinity. This is a very important characteristic because these copolymers possess relatively low glass transition temperatures and thus do not have the required crystallinity to achieve dimensional stability. During heat treatment (annealing) to purposefully mature the polymer morphology (possibly increase crystallinity levels), it was found that undesirable shrinkage occurred to varying degrees; reliable treatments could not be found to robustly produce acceptable foam product.

Additionally it has been found that lower levels of crystallinity result in a more rapid loss of mechanical properties due to faster hydrolysis of the polymer chains.

Donners et al. in commonly-assigned, co-pending U.S. patent application Ser. No. 14/728226 filed on evendate herewith and incorporated by reference, overcomes these limitations of low crystallinity by preparing Cap/Gly polymers utilizing a staged addition process thus creating glycolide end block capped polymers. This results in retaining a longer functional performance over time and better dimensional stability. However these kind of polymers are only soluble in sufficient concentrations in 1,4-dioxane within a limited range. In addition, the introduction of end blocks, while desirable for performance of the resulting device, leads to more rapid gel formation.

Accordingly, all attempts in the prior art to produce an acceptable medical foam from a gelled polymeric lyophilizing solution [changing freezing rate, drying temperature, etc.] did not result in a foam, let alone a foam useful for medical purposes. The resultant product may appear as a distorted film, not unlike the shape of a potato chip. Thus, specific processing conditions are needed to obtain a thoroughly frozen solution before gel formation occurs in order to achieve a proper foam.

Bioabsorbable films and film formation from bioabsorbable polymeric materials have also been described by various researchers over the years, e.g., U.S. Pat. No. 7,943,683 B2, "Medical Devices Containing Oriented Films of Poly-4-hydroxybutyrate and Copolymers"; U.S. Pat. No. 8,030, 434 B2, "Polyester Film, Process for Producing the Same and Use Thereof"; U.S. Pat. No. 4,942,087A, "Films of Wholly Aromatic Polyester and Processes for Preparation Thereof"; U.S. Pat. No. 4,664,859A, "Process for Solvent Casting a Film"; and, U.S. Pat. No. 5,510,176A, "Polytetrafluoroethylene Porous Film". Various conventional methodologies are known and exist to produce polymeric films. They include melt extrusion, solvent casting, and compression molding. Not all polymers can be easily converted to film products; additionally, different conversion techniques have different challenges. In the case of melt extrusion, the resin must be thermally stable, exhibiting an appropriate melt viscosity, i.e., not too low so as to cause "dripping" and not too high so as to develop excessively high pressures in the extruder, causing instability and non-uniform results. In the case of resins possessing low glass transition temperatures, the dimensional stability of the films made therefrom may be very low if the polymer morphology includes some chain orientation. This is a great driving force for shrinkage and distortion. To circumvent dimensional instability difficulties, the development of a certain amount of crystallinity in the film is advantageous. The rate of crystallization is important in establishing a robust film extrusion process, while the overall level of crystallinity is important in achieving dimensional stability and good mechanical properties. It is known that too low a crystallinity level will result in films which may distort upon ethylene oxide sterilization or upon exposure to even mildly elevated temperatures during processing, transportation, or storage. In a few surgical applications it is desirable for the final films to be strong with appropriate tear resistance, yet pliable enough to possess good handling characteristics.

An absorbable polymer used to manufacture films must possess certain melt and thermal properties, certain crystallization characteristics, as well as certain mechanical and hydrolysis properties, if it is to be suitable for fabricating surgical film products by the melt extrusion process. In the case of films made by solution casting, the polymer resin needs to possess appropriate solubility in a suitable solvent. Suitable solvents advantageously have an appropriate vapor pressure curve leading to suitable evaporation rates, and are generally non-toxic. The polymer must then possess certain solubility and crystallization characteristics, as well as certain mechanical and hydrolysis properties, if it is to be suitable for fabricating surgical film products by a solvent casting process.

Electrostatically spun nonwovens from absorbable polymeric materials are known in the art and have been described by various researchers. See for example U.S. Pat. No. 7,332,050 B2, "Electronic Spinning Apparatus, and a Process of Preparing Nonwoven Fabric Using the Same"; U.S. Pat. No. 7,934,917 B2. "Apparatus for Electro-Blowing or Blowing-Assisted Electro-Spinning technology"; and, U.S. Pat. No. 8,636,942 B2, "Nonwoven Fabric and Process for Producing the Same". One of the challenges present with electrostatically spun absorbable polymeric nonwovens is that the polymeric material must possess a number of particular characteristics. The polymer must possess adequate solubility in an appropriate solvent to create a suitable spinning dope. The rate of crystallization of the polymer must be appropriate to allow for a robust manufacturing process. The level of crystallinity that can be ultimately developed in the nonwoven fabric made of the polymer must be high enough so as to provide the fabric with appropriate dimensional stability. The level of crystallinity developed also influences the mechanical properties of the fabric. As pointed out earlier, crystallinity levels of the resin can be too high, making solubilization of the resin difficult. Crystallinity levels can also be too high in the fabric, made therefrom, negatively affecting mechanical properties and biological performance. There is a need in this art for novel polymers that provide sufficient mechanical properties long-term, post-implantation; and, novel polymers having glass transition characteristics that provide for softness in finished goods.

Melt-blown nonwoven constructs from absorbable polymeric materials are also known in this art. See for example U.S. Pat. No. 4,769,279A, "Low Viscosity Ethylene Acrylic Copolymers for Nonwovens"; U.S. Pat. No. 8,278,409 B2, "Copolymers of Epsilon-Caprolactone and Glycolide for Melt Blown Nonwoven Applications"; and, U.S. Pat. No. 8,236,904 B2, "Bioabsorbable Polymer Compositions Exhibiting Enhanced Crystallization and Hydrolysis Rates". One of the challenges with these constructs is that the polymeric material must possess a number of characteristics, including adequate melt viscosity, appropriate rates crystallization, and provide appropriate crystallinity in the finished goods. The polymers need to provide sufficient mechanical properties to the melt-blown constructs long-term, post-implantation, and also provide for softness in finished goods.

Accordingly, there is a need in the art for novel absorbable polymeric foams, films and nonwovens to be used in medical applications.

Specifically in the case of absorbable foams, there is a need to provide retention of mechanical properties post-implantation for extended periods of time, such 64 days or longer. Additionally, there is need to provide foams with improved dimensional stability to avoid warping, shrinking and other distortions during sterilization, storage, transportation, or an exposure to slightly elevated temperatures. Furthermore, there is a need to provide absorbable foams possessing appropriate stiffness, being neither too soft nor too hard, to allow good "spring-back" upon compression; this requires a proper range of crystallinity and $T_g$.

Further, there is a great need for an absorbable polymer that possesses high solubility characteristics in certain key solvents to avoid gelation during foam formation using the lyophilization method of manufacture.

Finally, there exists a need to provide an absorbable polymer possessing an adequate crystallization rate and the ability to achieve an adequate crystallization level so as to be able to form dimensionally stable foams by the lyophilization process, to form dimensionally stable films by a melt extrusion process, and to form dimensionally stable nonwoven fabrics by either electrostatic spinning or by melt blown processes.

SUMMARY OF THE INVENTION

Novel films and foams made from semi-crystalline, block copolymers of lactide and epsilon-caprolactone for long term absorbable medical applications are disclosed. The semicrystalline absorbable segmented copolymers, have repeating units of polymerized lactide and polymerized epsilon-caprolactone. The mole ratio of polymerized lactide to polymerized epsilon-caprolactone is between about 60:40 to about 75:25, and the copolymers possess a first heat $T_g$ as determined by differential scanning calorimetry at a scan rate of 10° C. per minute, equal to or less than 0° C., and a crystallinity level of about 25 percent to about 50 percent, as measured by wide angle X-ray diffraction.

Another aspect of the present invention is a method of making an absorbable foam by a melt process. The method has the steps of:

A. providing an absorbable polymer comprising a semicrystalline absorbable segmented copolymer, said copolymer comprising repeating units of polymerized lactide and polymerized epsilon-caprolactone, wherein the mole ratio of polymerized lactide to polymerized epsilon-caprolactone is between about 60:40 to about 75:25, said copolymer having a first heat Tg, as determined by differential scanning calorimetry at a scan rate of 10° C. per minute, equal to or less than 0° C., and a crystallinity level of about 20 to about 50 percent, as measured by wide angle X-ray diffraction, said copolymer having a melt temperature;

B. heating the copolymer above its melt temperature to form a melt;

C. introducing a suitable blowing agent (chemical or physical) into the melt; and, D. enabling the gas produced from the blowing agent to expand within the melt to form an absorbable foam.

Yet another aspect of the present invention is a method of making an absorbable foam by a melt process, having the steps of:

A. providing an absorbable polymer comprising a semi-crystalline absorbable segmented copolymer, said copolymer comprising repeating units of polymerized lactide and polymerized epsilon-caprolactone, wherein the mole ratio of polymerized lactide to polymerized epsilon-caprolactone is between about 60:40 to about 75:25, said copolymer having a first heat Tg, as determined by differential scanning calorimetry at a scan rate of 10° C. per minute, equal to or less than 0° C., and a crystallinity level of about 20 to about 50 percent, as measured by wide angle X-ray diffraction, said copolymer having a melt temperature;

B. transferring the said absorbable polymer to the hopper of a melt extruder outfitted with a profile die, with a barrel outfitted with a gas injection port, and die heated to a temperature within the range of about 10° C. above the melt temperature of said absorbable polymer to about 270° C. to form a melt;

C. extruding said absorbable polymer through said profile die, while injecting into the melt through the gas injection port a gas selected from the group of carbon dioxide, nitrogen, helium, and argon, resulting in a foam; and, D. collecting said foam at a rate to result in a foam thickness between about 0.1 mils and 50 mils.

A further aspect of the present invention is a method of making an absorbable foam by a melt process, comprising the steps of:

A. providing an absorbable polymer comprising a semi-crystalline absorbable segmented copolymer, said copolymer comprising repeating units of polymerized lactide and polymerized epsilon-caprolactone, wherein the mole ratio of polymerized lactide to polymerized epsilon-caprolactone is between about 60:40 to about 75:25, said copolymer having a first heat Tg, as determined by differential scanning calorimetry at a scan rate of 10° C. per minute, equal to or less than 0° C., and a crystallinity level of about 20 to about 50 percent, as measured by wide angle X-ray diffraction, said copolymer having a melt temperature;

B. transferring the said absorbable polymer in combination with a solid blowing agent to the hopper of a melt extruder outfitted with a profile die, and die heated to a temperature within the range of about 10° C. above the melt temperature of said absorbable polymer to about 270° C.;

C. extruding said absorbable polymer through said profile die, resulting in a foam; and, D. collecting said foam at a rate to result in a foam thickness between about 0.1 mils and 50 mils.

Still yet another aspect of the present invention is a method of making an absorbable foam by a lyophilization process. This process has the steps of:

A. providing an absorbable polymer comprising a semi-crystalline absorbable segmented copolymer, comprising repeating units of polymerized lactide and polymerized epsilon-caprolactone, wherein the mole ratio of polymerized lactide to polymerized epsilon-caprolactone is between about 60:40 to 75:25, said copolymer having a first heat Tg as determined by differential scanning calorimetry at a scan rate of 10° C. per minute, equal to or less than 0° C., and a crystallinity level of about 20 to about 50 percent, as measured by wide angle X-ray diffraction;

B. dissolving a sufficient quantity of the copolymer in a suitable solvent to form a lyophilizing solution;

C. pouring at least a part of the solution into a suitable mold; and,

D. subjecting the solution in the mold to a lyophilizing process to form an absorbable foam.

An additional aspect of the present invention is a lyophilizing solution. The solution has a solvent selected from the group consisting of 1,4-dioxane, trioxane, a mixture of at least 90 weight percent 1,4-dioxane and no more than 10 weight percent water, a mixture of at least 90 weight percent 1,4-dioxane and no more than 10 weight percent of an organic alcohol having a molecular weight of less than 1,500 Daltons. In addition, the lyophilizing solution of the present invention has about 3 wt. % to about 35 wt. % of a semicrystalline absorbable segmented copolymer, which possesses repeating units of polymerized lactide and polymerized epsilon-caprolactone, wherein the mole ratio of polymerized lactide to polymerized epsilon-caprolactone is between about 60:40 to 75:25, said copolymer having a first heat Tg as determined by differential scanning calorimetry at a scan rate of 10° C. per minute, equal to or less than 0° C., and a crystallinity level of about 20 to about 50 percent, as measured by wide angle X-ray diffraction.

Yet another additional aspect of the present invention is a method of making an absorbable film by melt processing. This process has the following steps:

A. providing an semicrystalline absorbable segmented copolymer, comprising repeating units of polymerized lactide and polymerized epsilon-caprolactone, wherein the mole ratio of polymerized lactide to polymerized epsilon-caprolactone is between about 60:40 to 75:25, said copolymer having a first heat Tg as determined by differential scanning calorimetry at a scan rate of 10° C. per minute, equal to or less than 0° C., and a crystallinity level of about 20 to about 50 percent, as measured by wide angle X-ray diffraction, said copolymer having a melt temperature;

B. transferring the said absorbable polymer to the hopper of a melt extruder outfitted with a slit die, with a barrel and die temperature within the range of about 10° C. above the melt temperature of the said absorbable polymer and about 270° C.;

C. extruding said absorbable polymer through said slit die, resulting in a film; and, D. drawing the film between about 0.8× to about 10× to form a film having a thickness between about 0.1 and 50 mils.

Yet another aspect of the present invention is a method of making an absorbable film by a solution process. The method has the steps of:

A. providing an absorbable polymer comprising a semi-crystalline absorbable segmented copolymer, said copolymer comprising repeating units of polymerized lactide and polymerized epsilon-caprolactone, wherein the mole ratio of polymerized lactide to polymerized epsilon-caprolactone is between about 60:40 to about 75:25, said copolymer having a first heat Tg, as determined by differential scanning calorimetry at a scan rate of 10° C. per minute, equal to or less than 0° C., and a crystallinity level of about 20 to about 50 percent, as measured by wide angle X-ray diffraction;

B. dissolving a sufficient quantity of the copolymer in a suitable solvent to form a polymer solution;

C. pouring at least a part of the solution into a suitable mold or dispensing the polymer solution onto a conveying surface; and, D. allowing the solvent to be removed from the polymer solution to form an absorbable film.

These and other aspects and advantages of the present invention will become more apparent from the following description and accompanying drawings.

BRIEF DESCRIPTION OF THE DRAWINGS

FIG. 1 is a plot of isothermal crystallization kinetics, as measured by Differential Scanning calorimetry, of the final inventive copolymers of Examples 1 and 3A.

FIG. 2 is histogram of sequence distribution results for the final inventive copolymers of Examples 1, 2A, 2B, 3A and 3B as measured by $^{13}$C NMR.

FIG. 3A is a photograph of three foam strips from Example 7 (10% w/w concentration) prior to exposure to a pH 7.27 phosphate buffered solution at 37° C.

FIG. 3B is a photograph of three foam strips from Example 7 (10% w/w concentration) after exposure to a pH 7.27 phosphate buffered solution at 37° C. for 28 days.

FIG. 3C is a photograph of three foam strips from Example 7 (10% w/w concentration) after exposure to a pH 7.27 phosphate buffered solution at 37° C. for 64 days.

FIG. 4A is a photograph of three foam strips from Example 8 (10% w/w concentration) prior to exposure to a pH 7.27 phosphate buffered solution at 37° C.

FIG. 4B is a photograph of three foam strips from Example 8 (10% w/w concentration) after exposure to a pH 7.27 phosphate buffered solution at 37° C. for 28 days.

FIG. 4C is a photograph of three foam strips from Example 8 (10% w/w concentration) after exposure to a pH 7.27 phosphate buffered solution at 37° C. for 64 days.

FIG. 5A is a photograph of three foam strips from Example 8 (20% w/w concentration) prior to exposure to a pH 7.27 phosphate buffered solution at 37° C.

FIG. 5B is a photograph of three foam strips from Example 8 (20% w/w concentration) after exposure to a pH 7.27 phosphate buffered solution at 37° C. for 28 days.

FIG. 5C is a photograph of three foam strips from Example 8 (20% w/w concentration) after exposure to a pH 7.27 phosphate buffered solution at 37° C. for 64 days.

FIG. 6A is a photograph of three foam strips from Example 9 (10% w/w concentration) prior to exposure to a pH 7.27 phosphate buffered solution at 37° C.

FIG. 6B is a photograph of three foam strips from Example 9 (10% w/w concentration) after exposure to a pH 7.27 phosphate buffered solution at 37° C. for 28 days.

FIG. 6C is a photograph of three foam strips from Example 9 (10% w/w concentration) after exposure to a pH 7.27 phosphate buffered solution at 37° C. for 64 days.

FIG. 7A is a photograph of three foam strips from 36/64 Caprolactone and Glycolide Comparator (10% w/w concentration) prior to exposure to a pH 7.27 phosphate buffered solution at 37° C.

FIG. 7B is a photograph of three foam strips from 36/64 Caprolactone and Glycolide Comparator (10% w/w concentration) after exposure to a pH 7.27 phosphate buffered solution at 37° C. for 28 days; each strip is contained in a vial.

FIG. 7C is a photograph of three foam strips from 36/64 Caprolactone and Glycolide Comparator (10% w/w concentration) after exposure to a pH 7.27 phosphate buffered solution at 37° C. for 64 days.

FIG. 8 is a photograph of two foam strips from 36/64 Caprolactone and Glycolide Comparator with endblocks (10% w/w concentration): The top foam was made using a lyophilization recipe with a "quench" freeze, allowing the solution to be cooled quickly so it freezes before a gel can form. The bottom foam was made without the quench step, which resulted in a failed foam that a) had high residual 1,4 dioxane levels, and b) had a warped "potato-chip"-like appearance.

FIG. 9 is a photograph of a failed foam strip prepared as a 4×4 inch sheet from 36/64 Caprolactone and Glycolide Comparator with endblocks (10% w/w concentration). This foam strip was made without using a "quench" freeze.

DETAILED DESCRIPTION OF INVENTION

As used herein, and for clarity purposes, a number of terms will be defined. A random (copolyester) copolymer is defined as a copolyester having a sequence distribution of the monomer moieties along the chain that is at least as random as a copolymer of that overall composition made from lactone monomers or hydroxy acids in which all the monomers are added in a single step to the polymerization reactor, as governed by reactivity ratio considerations at the time of the polymerization.

Statistical copolymers are copolymers in which the sequence of monomer residues follows a statistical rule. If the probability of finding a given type monomer residue at a particular point in the chain is equal to the mole fraction of that monomer residue in the chain, then the polymer may be referred to as a "truly random copolymer". In a random copolymer, the sequence distribution of monomeric units follows Bernoullian statistics.

Truly random copolymers are difficult to find due to the complications of the phenomena of monomer reactivity ratios. Although the monomers may be added to a batch reactor in a single step, there may be a slight propensity of one monomer adding to the growing chain over another monomer. This is discussed further below in this specification.

To form a random copolymer, in a batch polymerization process, the monomers are generally added to the batch reactor in a single step. In a continuous polymerization process, the monomers are added to the continuous reactor in a substantially constant composition.

A segmented (copolyester) copolymer on the other hand possesses a non-random sequence distribution beyond what would be expected based on reactivity ratio considerations that is less random than a random copolymer.

When the sequence length of a given monomer starts to get large, it begins to approach a blocky structure. A "block copolymer" can be multi-block in nature, tetrablock, triblock or diblock, depending on the number of different chemical blocks.

A block copolymer that is a "diblock copolymer" might have a structure containing two different chemical blocks and is then referred to as an A-B block copolymer. If a triblock copolymers has one monomer sequence, A, at its ends and a second, B, in its interior, it might be referred to an A-B-A block copolymer.

A known technique to produce a non-random sequence distribution in ring-opening polymerizations is the method of adding different monomer feeds to the reactor in stages. One might add an amount of monomer B to the reactor with a monofunctional initiator. A polymer is formed made of only B sequences. A second monomer, A, is then added to the reactor; the copolymer thus formed might then be an A-B block copolymer. Alternately, if a difunctional initiator is used at the start of the polymerization, the copolymer thus formed might then be an A-B-A block copolymer.

To help in characterizing the "blockiness" of the sequence distribution of a copolymer, Harwood (reference: Harwood, H. J.; Ritchey, W. M. Polymer Lett. 1964, 2, 601) disclosed a "run number" concept. For a copolymer made up of polymerized "A" repeat units and polymerized "B" repeat units, the corresponding run numbers reflect the average chain sequence length for the individual "monomers". In looking down the chain, every time an A unit was encountered, a counter was activated. Every time another A unit was observed, the counter was increased by one; the counter was stopped as soon as a B unit was reached. When the entire chain is sampled and the work completed on the rest of the resin, an average value can be established for the Harwood run number for the "A" unit. The same can be done for "B". Statistical treatments have shown that for a theoretically random copolymer of A/B molar composition, the Harwood run number for each of the components can be calculated based on the following equations:

$$HRN_A = 1 + ([A]/[B]) \text{ and } HRN_B = 1 + ([B]/[A]) \quad (1)$$

where $HRN_A$ and $HRN_B$ are the Harwood Run Numbers for repeat units A and B, respectively, [A] and [B] are the molar fractions of repeat units A and B, respectively.

Thus a 20/80 A/B random copolymer made up of A and B units is expected to have Harwood run numbers of 1.25 and 5.0 for A and B, respectively. In the case of non-random copolymers, it is possible to have a copolymer of the same 20/80 composition with a Harwood run number for the A component much higher than the 1.25 value displayed in the random copolymer, for instance 1.5 or 3. This is clearly indicative of a propensity of "A" units to be together, i.e., a blocky sequence distribution.

In a copolymerization, the monomers may not be sequenced exactly randomly due to a phenomenon in which there is a great propensity of "monomer 1" to add to a growing chain terminated in a "monomer 1 repeat unit" or a great propensity of monomer 1 to add to a growing chain terminated in a "monomer 2 repeat unit". The concept of reactivity ratios, $r_1$ and $r_2$, has been developed to describe the phenomena. Specifically, the Mayo-Lewis equation, also called the copolymerization equation in polymer chemistry describes the distribution of monomers in a copolymer. Taking into consideration a monomer mix of two components $M_1$ and $M_2$ and the four different reactions that can take place at the reactive chain end terminating in either monomer (M*) with their reaction rate constants k:

$$M_1^* + M_1 \xrightarrow{k_{11}} M_1 M_1^* \quad (2)$$

$$M_1^* + M_2 \xrightarrow{k_{12}} M_1 M_2^* \quad (3)$$

$$M_2^* + M_1 \xrightarrow{k_{21}} M_2 M_1^* \quad (4)$$

$$M_2^* + M_2 \xrightarrow{k_{22}} M_2 M_2^* \quad (5)$$

Reactivity ratios are defined as:

$$r_1 = (k_{11}/k_{12}) \quad (6)$$

$$r_2 = (k_{22}/k_{21}) \quad (7)$$

where $k_{11}$, $k_{12}$, $k_{21}$, and $k_{22}$ are the rate constants of the reactions shown in equations 2 through 5, respectively.

A statistical random copolymer is generally formed when the values of $r_1$ and $r_2$ are both equal to one. The reactivity ratio that corresponds to epsilon-caprolactone monomer adding to a chain terminated in a lactidyl moiety (i.e. polymerized L(−)-lactide sequence) has been experimentally determined to be 44 while L(−)-lactide monomer adding to a chain terminated in a caproyl moiety (i.e., polymerized epsilon-caprolactone sequence) has been determined to be 0.28. Since the two reactivity ratios are quite different, this then leads to copolymers with a slightly non-random sequence distribution, even when both monomers are added to the reactor together at the start of the polymerization.

For a given copolymer there are expected Harwood run numbers associated with each of the polymerized monomers, assuming the sequence is truly random in nature. There is also an experimentally determined average chain sequence length value for each of the components. Defined herein is a "Randomness Factor" for each of the polymerized monomers; it is abbreviated as $RF_x$, where x denotes the particular monomer under consideration. The $RF_x$ for monomer x is the ratio of the experimentally determined average sequence length and the corresponding Harwood Run Number.

For instance, in the 20/80 A/B random copolymer made up of A and B units described previously, if it was indeed statically random, the expected Harwood run numbers should be 1.25 and 5.0 for A and B, respectively. If experimentally it was found that the average chain sequence length values for components A and B were 1.88 and 8.50 respectively, then one could calculate an $RF_A$ value of 1.5 (=1.88/1.25) and an $RF_B$ value of 1.7 (=8.5/5.0). Again the "randomness factor" is calculated from the ratio of the experimentally determined average chain sequence length and the corresponding theoretical Harwood Run Number assuming a statistically random sequence distribution.

An example of a random (copolyester) copolymer made from lactone monomers is the copolymer made by combining of 70 moles of lactide and 30 moles of epsilon-caprolactone into a reactor and polymerizing the combination without introducing any additional monomer in a subsequent step. It should be noted that a random (copolyester) copolymer made from lactide and epsilon-caprolactone in the compositional range of 60/40 to 75/25 will possess only very low levels of crystallinity, i.e., be nearly amorphous. Such lactide/epsilon-caprolactone copolymers possessing low levels of crystallinity will be unsuitable for use as strong fibers due to a lack of dimensional stability in view of the high orientation needed to achieve high strength. It should also be noted that random (copolyester) copolymers of even moderate molecular weight, made from lactide and epsilon-caprolactone in the compositional range of 60/40 to 75/25, will possess glass transition temperatures greater than room temperature, leading to stiff articles.

An example of a non-random (copolyester) copolymer made from lactone monomers or hydroxy acids is one in which the monomers are added to the reactor sequentially. For example, in a first stage of the polymerization 70 moles of lactide and 30 moles of epsilon-caprolactone are added to the reactor and polymerize this mixture; after the subsequent formation of the "prepolymer", an additional portion of one of the monomers, or a third monomer, is added. The sequence distribution of monomers along the various chains is then purposefully controlled.

The copolymer useful in the practice of the present invention is semi-crystalline, while the prepolymer is amorphous. The prepolymer compositions being in the range of about 45/55 to about 30/70 and the final compositions about 60/40 to about 75/25, mole basis, L(−)-lactide/epsilon-caprolactone. It has been surprisingly and unexpectedly discovered that the copolymers useful in the practice of the present invention are semi-crystalline in nature with glass transition temperatures well below room temperature. One possible application for such polymers is in the production of novel, strong, soft, dimensionally stable foams, films, and nonwoven fabrics.

Poly(lactide) is a high glass transition ($T_g$ of 60° C. to 65° C.), semi-crystalline polyester. This material has a high elastic modulus and is thus quite stiff making it generally unsuitable for monofilament surgical sutures, as pointed out in U.S. Patent Application 2013-0236499 A1. The high (elastic) modulus exhibited by poly(lactide) also makes it unsuitable for foams that must be compressible with good recovery, as well as unsuitable for soft, body-conforming films, or nonwoven fabrics; such articles, made from poly (lactide), are just too stiff. In addition, poly(lactide) foams, films and nonwovens do not absorb quickly enough for many key surgical applications, i.e., they last too long in vivo. It has been found, however, that certain copolymers of lactide and epsilon-caprolactone are, surprisingly and unexpectedly, particularly useful for applications requiring both softness and a longer term mechanical property loss profile.

For instance, a 72/28 mole/mole poly(lactide-co-epsilon-caprolactone) copolymer [72/28 Lac/Cap] was prepared in a sequential addition type of polymerization starting with a first stage charge of lactide and epsilon-caprolactone charge (45/55 Lac/Cap mole percent) followed by a subsequent second stage of lactide addition only. The total initial charge was 75/25 mole/mole lactide/epsilon-caprolactone. Due to incomplete conversion of monomer-to-polymer and difference in reactivity, it is not uncommon to have the final (co)polymer composition differ slightly from the feed composition. The final composition of the copolymer was found to be 72/28 mole/mole lactide/epsilon-caprolactone. See Example 2A for the details of this copolymerization.

The present invention is directed toward medical devices in the form of foams, films and nonwoven fabrics made from copolymers of lactide and epsilon-caprolactone and methods of making such constructs. More specifically, this class of copolymers rich in lactide and made to have a blocky sequence distribution, that is non-random. In such lactide/epsilon-caprolactone copolymers in which the majority of the material is based on lactide, the morphology of the polymer needs to be optimized in order to be useful in long term applications. Appropriate polymer morphology is particularly important in implantable medical devices. We have discovered that such compositions must be rich in lactide, e.g., having a polymerized lactide content of 50 percent or greater.

Novel absorbable polymers have been, surprisingly and unexpectedly, discovered having a relatively narrow composition range and a non-random sequence distribution, which when made into foams, films and nonwoven fabrics will yield foams, films and nonwoven fabrics that are soft enough to have good handling characteristics, yet possess sufficiently effective mechanical integrity in vivo beyond 10 to 12 weeks post implantation. Segmented, that is, possessing a non-random sequence distribution beyond what would be expected based on reactivity ratio considerations, poly (lactide-co-epsilon-caprolactone) copolymers comprising a polymerized lactide having a molar level between 60 to 75 percent and a polymerized epsilon-caprolactone molar level between 25 to 40 percent are useful in the practice of the present invention. This class of copolymers, the poly(lactide-co-epsilon-caprolactone) family rich in lactide, preferably contains about 25 to about 35 mole percent of polymerized epsilon-caprolactone.

Specifically, poly(lactide-co-epsilon-caprolactone) copolymers rich in polymerized lactide having levels of incorporated lactide lower than about 60 mole percent are unsuitable for copolymers useful in the practice of the present invention because of crystallization difficulties. On the other hand, poly(lactide-co-epsilon-caprolactone) copolymers rich in polymerized lactide having levels of incorporated lactide greater than about 75 mole percent are unsuitable due to high modulus and absorption times that are too long.

The dimensional stability of foams, films and nonwoven fabrics used to manufacture surgical devices is very important to prevent shrinkage, both in the sterile package before use, as well as in the patient after surgical implantation. Dimensional stability in a low $T_g$ material can be achieved by crystallization of the formed article. Regarding the phenomena of crystallization of copolymers, a number of factors play important roles. These factors include overall chemical composition and sequence distribution. The dimensional stability of foams, films and nonwoven fabrics of the present invention is related to the ability of these articles to substantially maintain their physical dimensions even when exposed to slightly elevated temperatures, for example 36° C., and/or exposure to plasticizing gases such as ethylene oxide as may occur during sterilization. Although the overall level of crystallinity (and the $T_g$ of the material) plays a role in dimensional stability, it is important to realize that the rate at which the crystallinity is achieved is critical to processing. If a lower $T_g$ material is processed and its rate of crystallization is very slow, it is very difficult to maintain dimensional tolerances since shrinkage and warpage easily occur. Fast crystallization is thus an advantage. It has been discovered that for the systems at hand, in order to increase the rate of crystallization of a copolymer of given overall chemical composition, a block structure is preferable over a random sequence distribution. However, surprisingly and unexpectedly, it is now possible to achieve this with two lactone monomers, for instance lactide and epsilon-caprolactone, notwithstanding experimental difficulties and challenges due to transesterification and other factors.

Useful in the practice of the present invention, the compositional sequence of the inventive semi-crystalline copolymer is schematically illustrated as follows:

LLLLLLLLLLLLLL-CLCLCCLCLCLCCCLCLCCLC-LLLLLLLLLLLLLL

Polymerized Lactide Block-Polymerized (Lactide-co-epsilon-Caprolactone)-Polymerized Lactide Block with the semi-crystalline polylactide blocks representing approximately 45 to 70 weight percent of the copolymer and with the middle block formed from a nearly amorphous random prepolymer based on polymerized lactide and epsilon-caprolactone. In the above formula, L represents lactide, and C represents epsilon-caprolactone.

The novel copolymers useful in the practice of the present invention are prepared by first polymerizing the lactide and epsilon-caprolactone monomers at temperatures between about 170° C. and about 240° C. Temperatures between about 185° C. and about 195° C. are particularly advantageous. Although a monofunctional alcohol such as dodecanol might be used for initiation, a diol such as diethylene glycol has been found to work well. Combinations of mono-functional and di-functional, or multifunctional conventional initiators may also be used as a means of further influencing some important characteristics such as morphological development including crystallization rates and ultimate crystallinity levels. Reaction times can vary with catalyst level. Suitable catalysts include conventional catalysts such as stannous octoate. Sufficiently effective amounts of catalyst are utilized. The catalyst may be used at an overall monomer/catalyst level ranging from about 10,000/1 to about 300,000/1, with a preferred level of about 25,000/1 to about 100,000/1. After the completion of this first stage of the polymerization (e.g., 4 to 6 hours), the temperature is raised to above 200° C. (typically about 205° C. to 210° C.). Once the temperature is increased, for example to 205° C., the balance of lactide monomer can be added to the reactor; this can be conveniently done by pre-melting the monomer and adding it in a molten form. Once the second portion of lactide monomer is added, the temperature is brought to about 190° C. to about 200° C. to complete the co-polymerization (e.g., for about 1 to 2 hours).

It will be clear to one skilled in the art that various alternate polymerization approaches and parameters are possible to produce the copolymers of the present invention. For example, although not preferred, it may be possible to conduct all or part of the polymerizations without a catalyst present.

It is to be understood that the monomer feed added to the prepolymer may not necessarily need to be pure lactide. Instead of adding pure lactide monomer to the prepolymer, up to about ten mole percent of another monomer may be used to adjust the monomer feed added to the prepolymer. For instance, the monomer feed added to the prepolymer may contain minor amounts of epsilon-caprolactone; the monomer feed might be for instance 90/10 lactide/epsilon-caprolactone. Adding epsilon-caprolactone to the "end blocks" will lower the melting point, crystallization rate and overall crystallinity of the final copolymer. Adding more than about ten mole percent reduces properties too much to be useful for most applications. The compositional sequence of this variant of the inventive semi-crystalline copolymer is schematically illustrated as follows:

LLCLLLLLLLLCLL-CLCLCCLCLCLCCCLCLCCLC-LLLLLLLLCLLLLLL

In certain embodiments, it may be desirable to add minor amounts of glycolide to the monomer feed added to the prepolymer. For instance, the monomer feed added to the prepolymer may contain up to about ten mole percent glycolide; the monomer feed might be for instance 90/10 lactide/glycolide. Adding glycolide to the "end blocks" will lower the melting point, crystallization rate and overall crystallinity of the final copolymer, as well as increase the rate of absorption of the copolymer. Again adding more than about ten mole percent reduces properties too much to be useful for most applications. The compositional sequence of this variant of the inventive semi-crystalline copolymer is schematically illustrated as follows:

LLLLLGLLLLLLLL-CLCLCCLCLCLCCCLCLCCLC-LLLLGLLLLLGLLL

In the above formula, L represents lactide, and C represents epsilon-caprolactone, and G represents glycolide.

It is also to be understood that slight modification of the first stage prepolymer monomer feed composition can be adjusted to provide certain desired characteristics, all within the scope of the present invention. Thus other lactones such as p-dioxanone, trimethylene carbonate, or glycolide might be added to the lactide and epsilon-caprolactone mixture of the first stage. The amount of another monomer that is added in this first stage might be up to approximately, or about, 20 mole percent to adjust properties. For instance adding small amounts of glycolide to the lactide and epsilon-caprolactone in the first stage prepolymer monomer feed will decrease the breaking strength retention profile of a suture; this may occur without affecting the crystallization rate or overall crystallinity of the final copolymer. The compositional sequence of this variant of the inventive semi-crystalline copolymer is illustrated as follows:

LLLLLLLLLLLLLL-CLGLCCLCLCLCGCLCLCCGC-LLLLLLLLLLLLLL

Polymerization variations include the possibility of adding the "second stage" monomer to the prepolymer in multiple steps. Alternately, additional monomer may be added to the formed prepolymer in a continuous fashion over a short period of time, for instance 10 minutes or over a relatively longer period of time, for instance 2 hours.

Although adding all of the catalyst at the start of the polymerization is described herein, that is, at the start of the formation of the prepolymer, alternatively only a portion of the catalyst may be added in this stage of the polymerization, adding the remainder later, during the introduction of the monomer to the now formed prepolymer.

It is to be understood that that sufficiently effective amounts of acceptable coloring agents such as dyes and pigments might be added at any stage of the polymerization. Such colorants include D&C Violet No 2 or D&C Green No 6.

The present invention can be practiced using the L(−) isomer of lactide monomer, L(−)-lactide, or the D(+)isomer, D(+)-lactide. A mixture of the two monomers may be used, provided the resulting final copolymer crystallizes sufficiently to the extent needed to effectively provide dimensional stability. One may then use a isomer lactide monomer blend corresponding to 95 percent L(−)-lactide and 5 percent D(+)-lactide. Alternately, one may use a $^{50}/_{50}$ mixture of the L and D isomers [a racemic mixture], in combination with an appropriate level of epsilon-caprolactone to form the prepolymer, but use only L(−)-lactide [or D(+)-lactide] in the monomer feed to be introduced into the formed prepolymer. A copolymer so produced of the present invention will be semicrystalline in nature.

It is to be understood that low temperature polymerization techniques may also be used to make the copolymers of the present invention. As an example, the reaction is maintained at the melt reaction temperature for some period of time (e.g., about 3 to 4 hours), followed by the discharge of the reaction product into suitable containers for subsequent low temperature polymerization (e.g., 120° C.) for an extended period of time sufficient to effectively complete the co-polymerization. Higher monomer-to-polymer conversions may be possible utilizing this alternate low temperature finishing approach.

Again, one skilled in the art can provide a variety of alternate polymerization schemes to provide the novel copolymers of the present invention.

The novel copolymers useful in the practice of the present invention are semicrystalline in nature, having a crystallinity level ranging from about 25 to about 50 percent. They will have a molecular weight sufficiently high to allow the medical devices formed therefrom to effectively have the mechanical properties needed to perform their intended function. For melt blown nonwoven structures and microsphere formation, the molecular weights may be a little lower, and for conventional melt extruded fibers, they may be a little higher. Typically, for example, the molecular weight of the copolymers of the present invention will be such so as to exhibit inherent viscosities as measured in hexafluoroisopropanol (HFIP, or hexafluoro-2-propanol) at 25° C. and at a concentration of 0.1 g/dL between about 0.5 to about 2.5 dL/g. More typical inherent viscosities of the copolymer may range from about 0.8 to about 2.0 dL/g with preferred values ranging from 1.2 to about 1.8 dL/g, as measured in HFIP at 25° C. and at a concentration of 0.1 g/dL.

In one embodiment, medical devices made of the copolymers useful in the practice of the present invention may contain sufficiently effective amounts of conventional active ingredients or may have coatings containing such ingredients, such as antimicrobials, antibiotics, therapeutic agents, hemostatic agents, radio-opaque materials, tissue growth factors, and combinations thereof. In one embodiment the antimicrobial is Triclosan, PHMB, silver and silver derivatives, or any other bio-active agent.

The variety of therapeutic agents that may be used is vast. In general, therapeutic agents which may be administered via these medical devices and compositions of the present invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive or active ingredient, individual determinations may be made to determine the optimal dosage required. The determination of effective dosage levels to achieve the desired result will be within the realm of one skilled in the art. The release rate of the additives or active ingredients may also be varied within the realm of one skilled in the art to determine an advantageous profile, depending on the therapeutic conditions to be treated.

The copolymers useful in the practice of the present invention can be melt extruded by a variety of conventional means. Monofilament fiber formation can be accomplished by melt extrusion followed by extrudate drawing with or without annealing. Multifilament fiber formation is possible by conventional means. Methods of manufacturing monofilament and multifilament braided sutures are disclosed in U.S. Pat. No. 5,133,739, entitled "Segmented Copolymers of epsilon-Caprolactone and Glycolide" and U.S. Pat. No. 6,712,838 entitled "Braided Suture with Improved Knot Strength and Process to Produce Same", which are incorporated by reference herein in their entirety.

The copolymers useful in the practice of the present invention may be used to manufacture conventional medical devices in addition to sutures using conventional processes. For example, injection molding may be accomplished after allowing the copolymer to crystallize in the mold; alternately, biocompatible nucleating agents might be added to the copolymer to reduce cycle time. The copolymers of the present invention may be used to manufacture medical devices that function in part by being deformable without undergoing significant fracturing, cracking, splintering or other forms of breakage. Medical devices that function in part by being deformable include those that have hinges or are required to bend substantially. The medical devices may include (but are not limited to), conventional medical devices, especially implantable medical devices, including staples, tacks, clips, sutures, barbed sutures, tissue fixation devices, mesh fixation devices, anastomosis devices, suture and bone anchors, tissue and bone screws, bone plates, prostheses, support structures, tissue augmentation devices, tissue ligating devices, patches, substrates, meshes, tissue engineering scaffolds, drug delivery devices, and stents, etc.

The copolymers useful in the practice of the present invention may be used to produce inter-connected open cell porous foams by lyophilization. The lyophilization process is described as first dissolving the copolymers in a suitable solvent to prepare a homogeneous solution. Next, the polymer solution is subjected to a cooling thermal treatment that freezes the solution in order to achieve phase separation between the polymer and solvent components and locks in the pore morphology. It should be appreciated by those skilled in the art, that the solvent crystals form the eventual pore structure of the foam. The frozen polymer-solvent system then undergoes a vacuum drying cycle that removes the solvent by sublimation leaving the porous polymer structure. The vacuum drying cycle is typically performed at multiple temperatures. "Primary drying" occurs by sublimation at a temperature below the freezing point of the solvent; bulk solvent removal occurs during this process. Often a "secondary drying" above the freezing point of the solvent is used to remove any residual bound solvent by evaporation. It is advantageous to remove the majority of solvent during primary drying. This is because at temperatures above the freezing point of the solvent any significant amounts of remaining solvent could re-dissolve the polymer and disrupt the porous structure of the foam. This is often referred to as "melt-back" and can result in a product having a warped or "potato chip"-like appearance.

The solvents used for lyophilization should be selected for suitability for lyophilization (appropriate freezing temperatures, vapor pressure, etc.) and adequate polymer solubility. Solvents suitable for lyophilization include, but are not limited to, water, formic acid, ethyl formate, acetic acid, hexafluoroisopropanol (HFIP), cyclic ethers (i.e. TMF, DMF, and PDO), acetone, acetates of C2 to C5 alcohol (such as ethyl acetate and t-butylacetate), glyme (i.e. monoglyme, ethyl glyme, diglyme, ethyl diglyme, triglyme, butyl diglyme, and tetraglyme), methyl-ethyl ketone, dipropyleneglycol methyl ether, lactones (such as γ-valerolatcone, δ-valerolactone, β-butyrolactone, γ-butyrolactone), 1,4-dioxane, 1,3-dioxolane, 1,3-dioxolane-2-one (ethylene carbonate), dimethylcarbonate, benzene, toluene, benzyl alcohol, p-xylene, naphthalene, tetrahydrofuran, N-methyl pyrrolidone, dimethylformamide, chloroform, 1,2-dicholromethane, morpholine, dimethylsulfoxie, hexafluoroaceteone sesquihydrate (HFAS), anisole and mixtures thereof. Among these solvents, the preferred solvent of the present invention is 1,4-dioxane.

The polymer solution is typically dispensed into a mold prior to lyophilization for two purposes: 1) to provide containment of the liquid polymer solution for thermal treatment; and, 2) to provide a template for the shape of the resulting foam. The mold needs to have an opening to permit sublimation of the solvent. The mold can be made of any material that is compatible with the solvent system in order to maintain mold integrity throughout the process. It is often preferred that the mold is made of a material with a high thermal conductivity to facilitate the heat transfer to the polymer solution for the thermal treatment. The preferred mold materials for the present invention are aluminum and stainless steel.

Lyophilization for the present invention was carried out in a conventional tray-style freeze dryer (also known as a lyophilization unit). The unit comprises a cabinet with several shelves that can be heated and cooled by a refrigeration system. These shelves enable heating and cooling for the thermal treatment and drying cycles typically providing a shelf temperature range from −70° C. to 60° C. Polymer solutions can also be thermally treated in external cooling systems including but not limited to refrigerators, liquid nitrogen baths, and flash freezers. Thermal treatment can also include a step wherein after initially freezing the polymer solution, the temperature is raised above its Tg but below its freezing temperature to normalize the solvent ice crystal size through Oswalt ripening. The interior of the cabinet of the lyophilization unit is connected directly to a vacuum pump that reduces the ambient gas pressure in the cabinet and a condenser that collects the solvent vapor that is sublimated from the product on a surface that is typically cooled to −40° C. to −80° C. It should be appreciated by those skilled in the art that lyophilization could be performed in other conventional freeze dryer configurations including manifold and rotary freeze dryers.

The polymeric foams generated in this invention have interconnected and open cell porous structures. Pore sizes can range from about 10 microns to about 200 microns in diameter which typically result in the foams having an opaque white appearance. Foam density is directly associated with the concentration of the polymer solution and can typically range from about 0.03 mg/cc to about 0.30 mg/cc.

The novel foams made from the copolymers useful in the practice of the present invention may be used in medical applications as scaffolds for tissue engineering, buttress materials, defect or space fillers, wound healing dressing, 3D devices such as porous grafts, and other implantable wound healing, augmentation, and regeneration devices. The foams may have particular applications in bone or cartilage reengineering where the longer absorption times are preferred. The foams may be used in combination with other devices (such as meshes and other textiles) or additives that can be added during the lyophilization process. The foams may also be used as a drug delivery matrix whereby a therapeutic agent is mixed into the polymer solution before forming the foam or loaded into the foam after it is formed.

The films made from the copolymers useful in the practice of the present invention may be used in medical applications as tissue separating barriers, reinforcing buttress materials, and adhesion prevention. The films can be laminated with other devices (such as meshes and other textiles) to form multilayer structures.

It is to be understood that the copolymers useful in the practice of the present invention may be used to make fabrics via conventional melt blown nonwoven techniques. In addition, due to the expected good solubility in common organic solvents of the copolymers of the present invention, useful medical devices can be made by electrostatic spinning techniques. Similarly, the copolymers of the present invention may also be used to manufacture microcapsules and microspheres; these may be made to contain therapeutic agents for delivery to the patient.

It was found that the foam parts made from the copolymers useful in the practice of the present invention exhibited excellent dimensional stability during manufacture, during ethylene oxide sterilization, and upon storage of packaged products, especially compared to the random copolymers described in Vyakarnam, et al.

Surprisingly, despite possessing nonrandom molecular architecture, and high levels of crystallinity, it was found that the copolymers of Andjelic and Jamiolkowski in U.S. Patent Application 2013/0236499 A1 (incorporated by reference) unexpectedly do not exhibit gel formation overcoming some challenges in the lyophilization manufacturing processes presented by other copolymers, for example, the copolymers of Donners, et al.

Surprisingly, it was also found that substantially higher loading levels in at least one preferred solvent, 1,4-dioxane, can be achieved with the copolymers used in the foams, films, and methods of the present invention compared to their counterparts described in Vyakarnam, et al. and Donners, et al. Higher loading levels are valuable because the resultant foams will generally have higher mechanical properties compared with foams of lower bulk density.

Additionally, it was found that at a given bulk density, the copolymers useful in the practice of the present invention and the copolymers of Donners, et al. provide higher mechanical properties at a given foam bulk density due to the higher crystallinity that are achievable with these resins as compared to the copolymers described in Vyakarnam et al.

Most importantly, however, it was found that the inventive foams of the present application degrade at a much slower rate than those of Vyakarnam, et al. and Donners, et al. The extended mechanical property loss profiles exhibited post-implantation are very important in certain key surgical procedures. To be clear, the Vyakarnam, et al. foams exhibit zero residual strength under compression at approximately 25 days of in vitro treatment at 37° C. and pH 7.27 and the Donners et al. foams exhibit zero residual strength at approximately 40 days under the same in vitro testing conditions. Advantageously, the foams of the present invention last longer than 64 days.

In summary, the novel foams, films and processes of the present invention exhibit the following advantages over the prior art: lack gel formation leading to robust manufacturing processes while simultaneously providing moderate to high crystallinity levels in the foam; provide the possibility of higher loading levels; display higher mechanical properties due both to the higher crystallinity that are achievable at a given foam bulk density [based on the solids content of the solution to be lyophilized], as well to the higher bulk densities achievable due to the higher solution loading possible; good dimensional stability of the foam parts during manufacture, ethylene oxide sterilization, and storage; and finally, extended mechanical property loss profiles exhibited post-implantation.

The following examples are illustrative of the principles and practice of the present invention, although not limited thereto.

EXAMPLE 1

Synthesis of Segmented Block Copolymer Poly(L(−)-lactide-co-epsilon-caprolactone) at 64/36 by Mole [Initial Feed Charge of 70/30 Lac/Cap]

Using a conventional 2-gallon stainless steel oil-jacketed reactor equipped with agitation, 1,520 grams of epsilon-caprolactone and 1,571 grams of L(−)-lactide were added along with 3.37 grams of diethylene glycol and 2.34 mL of a 0.33M solution of stannous octoate in toluene. After the initial charge, a purging cycle with agitation at a rotational speed of 10 RPM in a downward direction was initiated. The reactor was evacuated to pressures less than 150 mTorr followed by the introduction of nitrogen gas. The cycle was repeated once again to ensure a dry atmosphere. At the end of the final nitrogen purge, the pressure was adjusted to be slightly above one atmosphere. The rotational speed of the agitator was reduced to 7 RPM in a downward direction. The vessel was heated by setting the oil controller at 190° C. When the batch temperature reached 110° C., rotation of the agitator was switched to an upward direction. The reaction continued for 4.5 hours from the time the oil temperature reached 190° C.

After the completion of the first stage portion of the polymerization, a very small amount of resin was discharged for analysis purposes; selected characterization was performed. The chemical composition of the prepolymer, as determined by NMR, was 45 mole percent polymerized lactide and 55 mole percent polymerized caprolactone with about 2 percent of residual unreacted monomer. The DSC data revealed that the prepolymer was fully amorphous with no crystallinity developed even after heat treatment. The glass transition temperature was determined to be −17° C. (minus 17° C.).

In the second stage portion of the polymerization, the heating oil controller set point was raised to 205° C., and 2,909 grams of molten L(−)-lactide monomer was added from a melt tank with the agitator speed of 12.5 RPM in a downward direction for 15 minutes. The agitator speed was then reduced to 7.5 RPM in the downward direction. The oil controller was then decreased to 200° C. and the reaction proceeded an additional 2.5 hours prior to the discharge.

At the end of the final reaction period, the agitator speed was reduced to 2 RPM in the downward direction, and the polymer was discharged from the vessel into suitable containers. Upon cooling, the polymer was removed from the containers and placed into a freezer set at approximately −20° C. for a minimum of 24 hours. The polymer was then removed from the freezer and placed into a Cumberland granulator fitted with a sizing screen to reduce the polymer granules to approximately 3/16 inches in size. The granules were sieved to remove any "fines" and weighed. The net weight of the ground and sieved polymer was 5.065 kg; the ground polymer was then placed into a 3 cubic foot Patterson-Kelley tumble dryer to remove any residual monomer.

The Patterson-Kelley tumble dryer was closed, and the pressure was reduced to less than 200 mTorr. Once the pressure was below 200 mTorr, the dryer rotation was activated at a rotational speed of 10 RPM with no heat for 18 hours. After the 18 hour period, the oil jacket temperature was set to 55° C. with drying at this temperature for 4 hours. The oil temperature was again raised, this time to 65° C.; this period lasted 2 hours. Two additional heating periods were employed: 85° C. for 12 hours, and 110° C. for 3 hours. At the end of the final heating period, the batch was allowed to cool for a period of 4 hours while maintaining rotation and vacuum. The polymer was discharged from the dryer by pressurizing the vessel with nitrogen, opening the discharge valve, and allowing the polymer granules to descend into waiting vessels for long term storage.

The long term storage vessels were air tight and outfitted with valves allowing for evacuation so that the resin was stored under vacuum. The dried resin exhibited an inherent viscosity of 1.27 dL/g, as measured in hexafluoroisopropanol at 25° C. and at a concentration of 0.10 g/dL. Gel permeation chromatography analysis showed a weight average molecular weight of approximately 60,000 Daltons. Nuclear magnetic resonance analysis confirmed that the resin contained 64 mole percent polymerized L(−)-lactide and 36 mole percent polymerized epsilon-caprolactone, with a residual monomer content of about 1.6 percent. The glass transition temperature, $T_g$, of the dried resin was −17° C., the melting point was 160° C., and the heat of fusion, $\Delta H_m$, was 26 J/g as determined by Differential Scanning calorimetry using the first heat scan and a heating rate of 10° C./min. Wide Angle X-ray Diffraction (WAXD) analysis revealed that the dried resin contains 34 percent of crystallinity.

EXAMPLE 2A

Synthesis of Segmented Block Copolymer Poly(L(−)-lactide-co-epsilon-caprolactone) at 72/28 by Mole [Initial Feed Charge of 75/25 Lac/Cap]

Using a conventional 10-gallon stainless steel oil-jacketed reactor equipped with agitation, 5,221 grams of epsilon-caprolactone and 5,394 grams of L(−)-lactide were added along with 13.36 grams of diethylene glycol and 9.64 mL of a 0.33M solution of stannous octoate in toluene. After the initial charge, a purging cycle with agitation at a rotational speed of 10 RPM in a downward direction was initiated. The reactor was evacuated to pressures less than 150 mTorr followed by the introduction of nitrogen gas. The cycle was repeated once again to ensure a dry atmosphere. At the end of the final nitrogen purge, the pressure was adjusted to be slightly above one atmosphere. The rotational speed of the agitator was reduced to 7 RPM in a downward direction. The vessel was heated by setting the oil controller at 190° C. When the batch temperature reached 110° C., rotation of the agitator was switched to the upward direction. The reaction continued for 6 hours from the time the oil temperature reached 190° C.

After the completion of the first stage portion of the polymerization, a very small amount of resin was discharged for analytical purposes; selected characterization was performed. The chemical composition of the prepolymer was the same as in Example 1: 45/55 Lac/Cap mole percent with about 2 percent of residual monomer as determined by NMR. The DSC data revealed that the prepolymer was fully amorphous with no crystallinity developed, even after heat treatment. The glass transition temperature was again determined to be −17° C. (minus 17° C.).

In the second stage, the oil controller set point was raised to 205° C., and 14,384 grams of molten L(−)-lactide monomer was added from a melt tank with an agitator speed of 12.5 RPM in a downward direction for 15 minutes. The agitator speed was then reduced to 7.5 RPM in the downward direction. The oil controller was then decreased to 190° C. and the reaction proceeded an additional 3 hours prior to the discharge. At the end of the final reaction period, the agitator speed was reduced to 2 RPM in the downward direction, and the polymer was discharged from the vessel into suitable containers.

The resin was divided into two portions. A minor portion of the divided resin was treated as described in Example 2B. The major portion of the copolymer, 13,930 grams, was subjected to the same grinding, sieving and drying steps described in Example 1 using the following heat/drying treatment: 12 hours at 25° C., 4 hours at 55° C., 4 hours at 75° C., and 12 hours at 110° C., respectively.

The dried resin exhibited an inherent viscosity of 1.52 dL/g, as measured in hexafluoroisopropanol at 25° C. and at a concentration of 0.10 g/dL. Gel permeation chromatography analysis showed a weight average molecular weight of approximately 79,000 Daltons. Nuclear magnetic resonance analysis confirmed that the resin contained 72 mole percent polymerized L(−)-lactide and 28 mole percent polymerized epsilon-caprolactone with a residual monomer content of about 1.5 percent. The glass transition temperature, $T_g$, of the dried resin was −8° C., the melting point was 169° C., and the heat of fusion, $\Delta H_m$, was 33 J/g as determined by Differential Scanning calorimetry using the first heat scan procedure and the heating rate of 10° C./min. Wide Angle X-ray Diffraction (WAXD) analysis revealed that the dried resin contained 43 percent crystallinity.

EXAMPLE 2B

Synthesis of Segmented Block Copolymer Poly(L(−)-lactide-co-epsilon-caprolactone) at 74/26 by Mole [Initial Feed Charge of 75/25 Lac/Cap, Solid-state Polymerization Final Treatment]

The smaller portion of the discharged resin, 6,900 grams, produced and described in Example 2A above was placed in a nitrogen purged oven and heated for 72 hours at 120° C. This solid state polymerization step was conducted in order to further increase the monomer conversion. After the solid state polymerization treatment, the resin was ground, sieved, and dried using the same procedures described earlier in Examples 1 and 2A.

The dried resin exhibited an inherent viscosity of 1.58 dL/g, as measured in hexafluoroisopropanol at 25° C. and at a concentration of 0.10 g/dL. Gel permeation chromatography analysis showed a weight average molecular weight of approximately 83,000 Daltons. Nuclear magnetic resonance analysis confirmed that the resin contained 74 mole percent polymerized L(−)-lactide and 26 mole percent polymerized epsilon-caprolactone with a residual monomer content of about 1.0 percent. The glass transition temperature, $T_g$, of the dried resin was −8° C., the melting point was 168° C., and the heat of fusion, $\Delta H_m$, was 39 J/g as determined by Differential Scanning calorimetry using first heat data and a heating rate of 10° C./min. Wide Angle X-ray Diffraction (WAXD) analysis revealed that the dried resin was 43 percent crystalline.

EXAMPLE 3A

Synthesis of Segmented Block Copolymer Poly(L(−)-lactide-co-epsilon-caprolactone) at 74/26 by Mole [Initial Feed Charge of 75/25 Lac/Cap]

Using a conventional 10-gallon stainless steel oil jacketed reactor equipped with agitation, 5,221 grams of epsilon-caprolactone and 2,826 grams of L(−)-lactide were added along with 9.65 grams of diethylene glycol and 9.64 mL of a 0.33M solution of stannous octoate in toluene. The reactor's conditions were identical those in Example 2A, except that the reaction in the first stage lasted for 4 hours from the time the oil temperature reached 190° C.

After the completion of the first polymerization stage, a very small amount of resin was discharged for analysis purposes; selected characterization was performed. The chemical composition of the prepolymer in this case was 30/70 Lac/Cap mole percent with about 3 percent of residual monomer as determined by NMR. The DSC data revealed that the prepolymer was fully amorphous with no crystallinity developed even after heat treatment. The glass transition temperature was found to be lower than that in Examples 1 and 2A, −39° C. (minus 39° C.), most likely due to the higher epsilon-caprolactone content present in the first stage.

In the second stage, the oil controller set point was raised to 205° C., and 16,953 grams of molten L(−)-lactide monomer was added from a melt tank. The oil controller was then decreased to 200° C. and the reaction continued an additional 3 hours prior to the discharge.

The major portion of the copolymer, 13,870 grams, was subjected to the same grinding, sieving and drying steps described in Example 1 using the following heat/drying treatment: 12 hours at 25° C., 4 hours at 55° C., 4 hours at 75° C., and 12 hours at 110° C. (the same conditions as for Example 2A).

The dried resin exhibited an inherent viscosity of 1.63 dL/g, as measured in hexafluoroisopropanol at 25° C. and at a concentration of 0.10 g/dL. Gel permeation chromatography analysis showed a weight average molecular weight of approximately 90,000 Daltons. Nuclear magnetic resonance analysis confirmed that the resin contained 74 mole percent polymerized L(−)-lactide and 26 mole percent polymerized epsilon-caprolactone with a residual monomer content of about 1.5 percent. The glass transition temperature, $T_g$, of the dried resin was −34° C., the melting point was 170° C., and the heat of fusion, $\Delta H_m$, was 35 J/g, as determined by Differential Scanning calorimetry using the first heat data and a heating rate of 10° C./min. Wide Angle X-ray Diffraction (WAXD) analysis revealed that the dried resin was 45 percent crystalline.

EXAMPLE 3B

Synthesis of Segmented Block Copolymer Poly(L(−)-lactide-co-epsilon-caprolactone) at 76/24 by Mole [Initial Feed Charge of 75/25 Lac/Cap, Solid-state Polymerization Final Treatment]

The smaller portion of the discharged resin, 8,500 grams, produced and described in Example 3A, was placed in a nitrogen purged oven and heated in a solid state fashion for 72 hours at 120° C. This step was conducted in order to further increase the monomer conversion. After the solid state polymerization treatment, the resin was ground, sieved, and dried using the same procedures described earlier in earlier examples.

The dried resin exhibited an inherent viscosity of 1.70 dL/g, as measured in hexafluoroisopropanol at 25° C. and at a concentration of 0.10 g/dL. Gel permeation chromatography analysis showed a weight average molecular weight of approximately 91,000 Daltons. Nuclear magnetic resonance analysis confirmed that the resin contained 76 mole percent polymerized L(−)-lactide and 24 mole percent polymerized epsilon-caprolactone with a residual monomer content of about 1.0 percent. The glass transition temperature, $T_g$, of the dried resin was −34° C., the melting point was 170° C., and the heat of fusion, $\Delta H_m$, was 49 J/g, as determined by Differential Scanning calorimetry using the first heat data and a heating rate of 10° C./min. Wide Angle X-ray Diffraction (WAXD) analysis revealed that the dried resin was 50 percent crystalline.

EXAMPLE 4

Selected Properties of Copolymers of the Present Invention
a) Differential Scanning Calorimetry (DSC) and Melt Index (MI) Characteristics DSC measurements were conducted using a model Q20-3290 calorimeter from TA Instruments (New Castle, Del.) equipped with automatic sampler. In individual experiments, the dried, heat treated copolymer resins as described in Examples 1, 2A, 2B, 3A, and 3B were placed into DSC pans, quenched below −60° C., and heated at the constant heating rate of 10° C./min to determine their calorimetric properties (first heat properties); these included the glass transition temperature, $T_g$, the melting point, $T_m$ and the heat of fusion, $\Delta H_m$. From the second heat measurements (resin was melted at 200° C. and then quenched below −60° C.), values for $T_g$, $T_m$, $T_c$ (crystallization temperature), and $\Delta H_m$ were obtained that are independent from the previous heat treatment history. Data obtained using calorimetry and melt index measurements are displayed in Table 1.

TABLE 1

Melt Index, MI and DSC Results during the First and Second Heat Runs on the Copolymers of the Present Invention

| | | First heat, DSC | | | Second heat, DSC | | |
|---|---|---|---|---|---|---|---|
| Example | MI (g/10 min) | $T_g$ (° C.) | $T_m$ (° C.) | $\Delta H_m$ (J/g) | $T_g$ (° C.) | $T_c/T_m$ (° C.) | $\Delta H_m$ (J/g) |
| 1 | 0.224 | −17 | 160 | 26 | 12 | 106/160 | 21 |
| 2A | 0.066 | −8 | 169 | 33 | 29 | 125/168 | 25 |
| 2B | 0.052 | −8 | 168 | 39 | 33 | 128/168 | 24 |
| 3A | 0.016 | −34 | 170 | 35 | −32 & 53 | 124/169 | 28 |
| 3B | 0.018 | −34 | 170 | 49 | −35 & 53 | 125/168 | 29 |

The results in Table 1 indicated that the resin of Example 1 exhibited a lower overall crystallinity level (lower $\Delta H_m$ value), and a lower melting point than the rest of the examples. This is most likely due to a higher polymerized epsilon-caprolactone content present in this copolymer (36 mole percent) compared to the other resins. As noted before, the resin of Example 1 also has lower weight average molecular weight and IV. With an increase in polymerized lactide level in the structure (Examples 2A-B, 3A-B), the level of crystallinity increases (higher $\Delta H_m$ values), as well as the melting point values. It is very important to note that in all cases only a single $T_g$ was observed after the first heating scans. The $T_g$ values were all well below room temperature, ranging from minus 8° to minus 34° C.; low $T_g$ values may contribute to increased softness of medical devices produced from these materials.

Melt Index (MI) is used as a measure of the melt viscosity of the resins. MI experiments on dried resins of present invention were conducted using an Extrusion Plastometer, Tinius Olsen (Willow Grove, Pa., USA) at 175° C. with the nominal weight of 2,060 g. The die used in the MI measurements had a capillary with a diameter of approximately 0.023 inches and a length 0.315 inches. The MI data (second column in Table 1) indicate the lowest melt viscosity for Example 1, and the highest for Examples 3A and 3B, which is in agreement with the molecular weight and IV data mentioned earlier.

In order to gain preliminary information on potential fiber characteristics, the copolymers of the present invention were extruded through the Melt Index apparatus (at 215° C.), unoriented fiber parts collected, and then subjected to manual heat or cold drawing process until the fibers were fully stretched. Pieces of drawn fibers were examined for handling purposes only. It was found that fibers from all resins from the present invention (Examples 1 to 3B) showed good pliability and softness suitable for making monofilaments.

b) Isothermal Crystallization Kinetics by DSC

Crystallization characteristics were assessed. Isothermal crystallization kinetics of the polymers of the present invention were conducted using the Differential Scanning calorimetry techniques. The dried, heat-treated copolymer resins, as described in Examples 1, 2A, 2B, 3A, and 3B were placed into a DSC pan and completely melted at 200° C. for 2 minutes to remove any nucleation sites present in the sample. Subsequently, tested materials were rapidly cooled/quenched (rate −65° C./min) to the desired crystallization temperatures. The isothermal method assumes that no crystallization occurs before the sample reaches the test temperature; the data obtained supported this assumption. Crystallization behavior of the five samples was characterized over a wide range of temperatures, between 40° C. and 130° C. Isothermal crystallization kinetics (at constant temperature) were monitored as a change in heat flow as a function of time. The isothermal heat flow curve was integrated to determine the crystallinity parameters. It is worth noting that the isothermal DSC runs were made in randomized order to avoid any bias.

The development of crystallinity with time can be accessed from the degree of crystallization, α, which is expressed by the ratio $$\alpha = \frac{\Delta Ht}{\Delta H\infty} = \frac{\int_0^t \frac{dQ}{dt} dt}{\int_0^\infty \frac{dQ}{dt} dt} \tag{8}$$

where dQ/dt is the respective heat flow; $dH_t$, the partial area between the DSC curve and the time axis at time t; and $dH_\infty$, the total area under the peak and corresponds to the overall heat of crystallization. The degree of crystallization, α, is then the crystalline volume fraction developed at time t.

After performing the integration of the heat flow/time curve, the crystallization half-time, $t_{1/2}$, can be determined. The crystallization half-time is the time needed to reach 50 percent crystallinity of the total amount developed during the isothermal run. In order to express crystallization kinetics, a reciprocal crystallization half-time was presented as a function of crystallization temperature. These data are shown in FIG. 1 for resins of Examples 1 and 3A. The resins 2A, 2B, and 3B were also examined; both 2A and 2B samples show very similar trend as Example 1. The resins 3A, 3B behaved nearly identically to each other. Several important points can be drawn from the data in FIG. 1. Firstly, all examined resins showed a fast crystallization rate over a wide range of temperatures, especially when compared to random copolymers of the same composition. Fastest kinetics for the examined resins were observed at approximately 95° C.

Interestingly, the plot of Example 1 (FIG. 1) showed an unusual, second maximum at lower crystallization temperature (around 65° C.); the resins of Examples 2A and 2B displayed a second maximum at the same temperature as well. This information may be very useful, for instance, for optimizing extrusion conditions to increase crystallization efficiency during the drawing process. On the other hand, the samples 3A and 3B did not exhibit this lower temperature maximum; here, only a regular bell-shaped curve was observed with the crystallization rates similar to those of Example 1. The lack of a low temperature maximum in FIG. 1 for 3A and 3B resins may possibly be due to higher second heat $T_g$ values for these copolymers as previously reported in Table 1.

EXAMPLE 5

Hydrolysis Profile Data—Comparison with Poly(p-dioxanone)

The absorbability of the resins of the subject invention was assessed by an in vitro method. The method was found suitable for estimating synthetic absorbable polyester in vivo degradation time. Essentially, the article to be tested is subjected to hydrolysis at a given test temperature and a constant pH. Using pH-stat technology, a solution of weak base is added to the test article in an aqueous environment and the amount of base added as a function of time is recorded. In vivo absorption time is compared to the generated in vitro data, initially with model compounds and a number of commercially available absorbable products to establish a correlation curve.

In vitro absorption time was measured by an automated titration unit (718 Stat Titrino, Brinkmann, Westbury, N.Y., USA) at 70° C., under constant pH (7.3) in 70 mL of deionized (DI) water using 0.05N NaOH as a base. The weight of materials was about 100 mg. All of the polymer samples were in granular form with 6 pieces chosen for each resin having similar shape and size.

Hydrolysis data indicated that all examined materials hydrolyzed under the test conditions with the rate of disappearance of the copolymers of the present invention being slower than the control sample, poly(p-dioxanone) homopolymer. Hydrolysis results are presented in Table 2 in a form of hydrolysis half-time. Hydrolysis half-time is defined as time needed to hydrolyze half of the ester groups originally present. Shorter times suggest faster hydrolysis and vice versa.

TABLE 2

Hydrolysis Profile Data of Poly(p-dioxanone), PDS Dried Resin and the Final, Heat Treated Copolymers of the Present Invention

| Example | Composition (mole %) | Resin Shape & Size (# of pieces and total weight) | % C by WAXD | Did Hydrolysis Occur? | Hydrolysis half-time, $t_{1/2}$ (hours) |
|---|---|---|---|---|---|
| 1 | 64/36 Lac/Cap | Granular, 6 pieces, 96 mg | 34 | Yes | 300 |
| 2A | 72/28 Lac/Cap | Granular, 6 pieces, 96 mg | 43 | Yes | 240 |
| 3A | 74/26 Lac/Cap | Granular, 6 pieces, 97 mg | 45 | Yes | 260 |
| PDS | 100% PDO | Granular, 6 pieces, 97 mg | 55 | Yes | 100 |

It is evident from Table 2 that the inventive copolymers of Examples (1, 2A, and 3A) all exhibited a slower hydrolysis rate than the poly(p-dioxanone) homopolymer control, despite the fact that they exhibited lower levels of crystallinity.

EXAMPLE 6

Determination of the Average Chain Sequence Length (ACSL) of the Segmented Poly(L(−)-lactide-co-epsilon-caprolactone) Segmented Block Copolymers The copolymers described in the Examples 1, 2A, 2B, 3A and 3B were subjected to $^{13}$C NMR analysis (UNITYplus, Varian 400 MHz NMR system) to experimentally determine an average chain sequence length, ACSL for caproyl and lactidyl blocks ($ACSL_{Cap}$ and $ACSL_{LL}$, respectively). The peak assignments and method analysis used were based on the work reported earlier on a similar class of copolymers (Z. Wei et al./Polymer 50 (2009) 1423-1429). Listed in Table 3 are the final compositions (polymerized lactide/epsilon-caprolactone mole ratio), the $ACSL_{LL}$ and $ACSL_{Cap}$ values, the random factors for polymerized lactide and epsilon-caprolactone, $RF_{LL}$ and $RF_{Cap}$, respectively for the final copolymers of Examples 1, 2A, 2B, 3A and 3B as well as some comparative prior art copolymers. Comparative Copolymer X is a melt prepared random copolymer reported by Wei et al. in 2009 (Z. Wei et al./Polymer 50 (2009) 1423-1429); Comparative Copolymer Y is a solution prepared random copolymer reported by Vanhoorne, et al. in 1992 (Vanhoorne, et al./Macromolecules 25 (1992) 37-44; and Comparative Copolymer Z is a melt prepared block copolymer reported by Baimark, et al. in 2005 (Journal of Materials Science: Materials In Medicine 16 (2005) 699-707).

TABLE 3

$^{13}$C NMR Data on the Polymers of the Present Invention

| Example | Final Composition Lac/ε-Cap (mole %) | $ACSL_{LL}$ | $ACSL_{Cap}$ | $RF_{LL}$ | $RF_{Cap}$ |
|---|---|---|---|---|---|
| 1 (34% cryst.) | 64/36 | 6.7 | 3.3 | 2.41 | 2.11 |
| 2A (43% cryst.) | 72/28 | 7.3 | 2.3 | 2.04 | 1.66 |
| 2B (43% cryst.) | 74/26 | 7.4 | 2.2 | 1.92 | 1.63 |
| 3A (45% cryst.) | 74/26 | 11.1 | 3.1 | 2.89 | 2.29 |
| 3B (50% cryst.) | 76/24 | 10.8 | 3.3 | 2.59 | 2.51 |
| Comparative Copolymer X (random) | 64/36 | 4.6 | 2.4 | 1.66 | 1.54 |
| Comparative Copolymer Y (random) | 70/30 | 5.1 | 2.2 | 1.53 | 1.54 |
| Comparative Copolymer Z (block) | 79/21 | 8.2 | 2.3 | 1.72 | 1.82 |

Data in Table 3 indicate that for inventive Examples 1, 2A, 2B, 3A, and 3B, the average chain sequence lengths, ACSL, for caproyl and lactidyl blocks ($ACSL_{Cap}$ and $ACSL_{LL}$, respectively), are relatively long vs. the comparative polymers of similar compositions. Shown in FIG. 2 are the relative proportions, on a mole basis, of a variety of 3-member, 4-member, and 5-member sequence combinations; specifically, CCC, LLCC, CCLL, LLCLL, LLLLC, CLLC, CLLLL, and LLLLL. A particularly important sequence combination is the 5-member LLLLL, as it reflects the relative amount of crystallizable lactide in the copolymer, resulting in increased crystallizability and consequently dimensional stability of articles formed therefrom.

The randomness factors for the lactidyl blocks ($RF_{LL}$) of the inventive Examples, as shown in Table 3, are particularly large values. Having high randomness factor parameters indicates much higher blockiness of the lactide sequences in the inventive samples than the comparative examples. A consequence of possessing a high level of blockiness in the copolymers of the current invention is enhanced crystallization rates and ultimate crystallinity levels will be enhanced, leading to better fiber properties.

EXAMPLE 7

Foam Formation by Lyophilization of the Resin of Example 1
a) Solution Preparation
Solutions were prepared by weighing out 20 grams of the polymer of Example 1 and 180 grams of anhydrous 1,4-dioxane to achieve a 10% (w/w) solution concentration. The two components were combined in an Erlenmeyer flask, which was then fitted with a stir bar and placed in a water bath. The solution was heated at 70° C. with agitation for 1 to 2 hours. After removal from heat, the solution was then filtered through an extra course filter under gentle nitrogen pressure.

A sample of solution was then taken to measure the concentration via dry weight measurement. After recording the weight of the solution, the 1,4-dioxane was removed by allowing it to evaporate overnight and then subsequently dried in a vacuum oven heated to 50° C. for 48 hrs. The concentration of the solution was measured to be 10.1% (w/w).

b) Lyophilization

Lyophilization of the polymer solution into a foam construct was carried out in a LyoStar3 unit manufactured by SP Scientific.

Prior to lyophilization, the solution was heated to 75° C. for approximately 1 hour. The hot polymer solution was dispensed into a stainless steel mold having 30 cavities; each cavity had a configuration of a strip that was approximately 10 mm×60 mm×3 mm. Once filled, the mold was immediately placed into the lyophilization unit chamber that was preset to a temperature of −45° C. The lyophilization cycle was then initiated as specified by a computer controlled process steps (recipe). The recipe was comprised of the following sequences:

1. Thermal Treatment: The chamber was held at −45° C. for 1 hr and then ramped to 3° C. at a rate of 1° C./min. The unit was then held at 3° C. for 1 hr and then ramped back to −45° C. at a rate of −0.5° C./min for a hold of 1 hr.
2. Evacuation then commenced by pulling vacuum to 450 mTorr. Once that level was achieved, the unit was held at −45° C. for 2 hrs.
3. Drying was then started by ramping the unit to −10° C. at a rate of 0.5° C./min and held for 9 hrs. The vacuum level was then decreased to 20 mTorr and the shelf temperature was increased to 10° C. at a rate of 0.25° C./min and held for 2 hrs. The shelf temperature was then increased to 20° C. at a rate of 2° C./min and kept at that level until the cycle was stopped and vacuum was broken with nitrogen.

Following lyophilization, the foam strips were removed from the molds and stored under nitrogen until further use.

b) Annealing

Annealing was conducted under nitrogen using a Thermal Product Solutions Blue M Oven (Model No: DCI-296-G-G-MP750). Foams were placed on the shelf of the oven without any fixation. After purging the unit with nitrogen for 1 hour, the temperature of the oven was ramped to 90° C. and held there for 6 hours before returning to room temperature. After annealing, the foam strips were stored under nitrogen until further use.

EXAMPLE 8

Foam Formation by Lyophilization of the Resin of Example 2A a) Solution Preparation Two separate solutions were prepared with 10% and 20% (w/w) concentrations. For the 10% solution, 20 grams of the polymer of Example 2A and 180 grams of anhydrous 1,4-dioxane were weighed out. For the 20% solution, 40 grams of the same polymer and 160 grams of anhydrous 1,4-dioxane were weighed out. The components for each solution were combined in separate Erlenmeyer flasks, which were then fitted with a stir bar and placed in separate water baths. Solutions were heated at 80° C. with agitation for 1 to 2 hours. After removal from heat, the solutions were then filtered through an extra course filter under gentle nitrogen pressure.

A sample of solution was then taken to measure the concentration via dry weight measurement. After recording the weight of the solution, the 1,4-dioxane was removed by allowing it to evaporate overnight and then subsequently dried in a vacuum over heated to 50° C. for 48 hrs. The concentrations of the 10% and 20% solutions were measured to be 10.2% and 21.4% (w/w), respectively.

b) Lyophilization

Lyophilization of the polymer solutions into a foam construct was carried out as described in Example 7 above.

c) Annealing

Annealing of the foams was carried out as described in Example 7 above.

EXAMPLE 9

Foam Formation by Lyophilization of the Resin of Example 3A

Foams were prepared with the polymer of Example 3A using identical solution preparation, lyophilization, and annealing as described in Example 8 above. The measured concentration of the solution was 10.3% (w/w).

EXAMPLE 10

Subjective Mechanical Property Description of Foam

The four foams produced in Examples 7, 8, and 9 were white in appearance and smooth to the touch. All maintained their integrity after repeated manual bending and compression procedures. The foam made in Example 7 exhibited very good recovery to its original form after compression. The foams made with the 10% and 20% solution in Example 8 showed different physical properties. The 20% solution foam was nearly incompressible and could be described as "brick-like". The foam made with the 10% solution was compressible but did not exhibit complete recovery to shape after squeezing it like the foam in Example 7. The foam made in Example 9 had similar properties to the 10% solution foam from Example 8.

EXAMPLE 11

In Vitro Test Methods
Determination of Polymer Solubility in 1,4-Dioxane

The maximum solubility of a variety of absorbable polymers in 1,4-dioxane was evaluated by adding a given polymer resin in 1 g increments to 100 ml of 1,4-dioxane in a 250 ml roundbottom flask fitted with a nitrogen inlet adapter to maintain an inert atmosphere. The solution was heated to 85° C. and if the resin dissolved in less than 2 hrs another addition of 1 g polymer resin was made until either the solution formed a gel at elevated temperature or particulates remained after 2 hours of heating.

Determination of the Onset of Gelation

When gel formation occurs there is a distinct change in the viscosity of the solution. The onset of gelation time is therefore defined as the time point at which a large increase in solution viscosity occurs. In order to measure the onset time, 125 ml of solution prepared at 85° C. was placed in a 150 ml narrow beaker. The beaker was placed in a room temperature water bath which was positioned centrally under a Brookfield DVI-I⁺ viscometer fitted with a S62 spindle. The solution viscosity was measured at 10 rpm;

every 5-10 minutes (or more frequent if needed), a measurement was taken by averaging the viscosity over a 60 second interval. The resulting data is plotted and the onset time can be determined either graphically or by curve fitting methods.

A summary of the gelation times of some of the polymers of the present invention as well as some controls can be found in Table 4. Control 1-Random is a 64/36 random copolymer of glycolide and caprolactone, made by placing all of the reactants in the reactor at the start of the co-polymerization. Control 1-Block a 64/36 segmented block copolymer of glycolide and caprolactone, made by the process of sequential addition of monomers. Control 2-Block is similar to Control 1-Block with the exception of overall composition; it is a 75/25 segmented block copolymer of glycolide and caprolactone.

TABLE 4

Gelation Time of Polymers of the Present Invention and Controls

| Example | Composition (mole %) | Max. Concentration (wt. %) | Gelation time at 10 wt %, (min) |
|---|---|---|---|
| 1 | 64/36 Lac/Cap | 30% | >2880 |
| 2A | 72/28 Lac/Cap | 20% | >2880 |
| 3A | 74/26 Lac/Cap | 15% | >180 |
| Control 1-Random | 64/36 Gly/Cap | 24% | >180 but <1440 |
| Control 1-Block | 64/36 Gly/Cap | 14% | 14 |
| Control 2-Block | 75/25 Gly/Cap | <0.5% | Insoluble |

EXAMPLE 12

Subjective In Vitro Degradation Behavior of Foams from Examples 7, 8, and 9

The degradation behavior of all four foams from Examples 7, 8, and 9 were evaluated by assessing the integrity of the foams when exposed to a degradation media over time. Briefly, a single foam strip was placed in a 50 ml conical tube and immersed in 50 ml of a pH 7.27 phosphate buffered solution. The tube was then placed on a shaker table in a controlled environmental chamber at 37° C. The selected test conditions usually mimic what may occur in an in vivo environment. The shaker table provided gentle agitation throughout the duration of the study. Foam samples were examined periodically for structural integrity by aggressively shaking the tube imparting turbulence to the sample. The number of days submerged in buffer at 37° C. until the sample broke was recorded. This test was repeated three times for each foam. The results are presented in FIGS. 3A to 6C.

As a comparator, foam of a random copolymer of 36/64 caprolactone and glycolide (CAP/GLY) was prepared in an identical fashion as described in the foam preparation methods of Examples 7, 8, and 9 and subjected to the same test conditions as described above. FIG. 7A is a photograph of three foam strips from 36/64 Caprolactone and Glycolide Comparator made by 10% w/w concentration of solids prior to exposure to a pH 7.27 phosphate buffered solution at 37° C.

All foam samples, comparative and inventive, maintained integrity up to 24 days. On day 25, one of the foam strips made from the comparative 36/64 CAP/GLY random copolymer broke upon agitation of the tube. By day 28, the remaining two foams of this comparative 36/64 CAP/GLY random copolymer had fragmented as well; this is shown in the photograph in FIG. 7B. By day 64, the foam strips of the comparative 36/64 CAP/GLY random copolymer had extensively fragmented; this is shown in the photograph in FIG. 7C.

In contrast, all foams of the inventive segmented poly(L(−)-lactide-co-epsilon-caprolactone) block copolymers had maintained integrity through 28 days as shown in FIGS. 3B, 4B, 5B, and 6B.

The study was continued to 64 days where the foams of the inventive segmented poly(L(−)-lactide-co-epsilon-caprolactone) block copolymers maintained integrity. This is shown in the photographs in FIGS. 3C, 4C, 5C, and 6C. The test articles were removed from the buffer and handled with forceps without any breakage. While there was no direct measurement, there were no apparent changes in the dimensions of these foams. Again in contrast, the foam strips of the comparative 36/64 CAP/GLY random copolymer has been completely disrupted at 64 days (see FIG. 7C).

Finally, examples of absorbable polymer solutions that failed to lyophilize into acceptable foams are shown in the bottom article in FIG. 8 and the article of FIG. 9. These foams were made from a solution having 10 weight percent of the 36/64 Caprolactone and Glycolide copolymer having endblocks as described in Donners et al. The top foam in FIG. 8 was made using lyophilization with a "quench" freeze, in which the solution was cooled quickly before a gel can form. The bottom foam in FIG. 8 was made without the quench step, which resulted in a failed foam that had high residual 1,4-dioxane levels, and had a warped "potato-chip" like appearance. Similarly, FIG. 9 shows failed foam of the same material prepared as a 4×4 inch sheet. The procedure also did not include a "quench" freeze step, which as shown in Donners et al., is needed for the lyophilization of polymer solutions that exhibit gel formation but not needed for the polymers of the present invention.

EXAMPLE 13

Film Formation by Melt Extrusion of the Resin of Example 2A a) Melt Extrusion

The melt film extrusion of the resin of Example 2A of the present invention was carried out using a melt extruder Model KN125 manufactured by Davis Standard Corp., Pawcatuck, Conn. 06379, U.S.A, outfitted with a film die. A die gap of 6 mils was used in all film extrusion runs. Extruder temperatures throughout the different barrel zones ranged from 160 to 190° C., with the die temperature kept at 190° C. The screw speed was set to 10.9 rpm, while the linear speed of the pull out roll was maintained at 4.9 fpm. During film collection, a silicone release paper dispensed from a roll stand was used to separate the film layers being wound on the take-up roll. After extrusion, the film with corresponding silicone release paper was unrolled and cut to convenient lengths. The cut films were then stored under vacuum, sandwiched between silicone release paper, prior to further use. The thickness of the film was determined to be 3.0 mil.

b) Post-Treatment—Annealing

The extruded film of the resin of Example 2A of the present invention was additionally heat treated to mature the polymer morphology and to aid in the removal of any residual monomer regenerated during the melt processing. The thermal treatment (annealing) was found to increase the crystallinity level, which is then expected to improve the dimensional stability of the film samples. Annealing was conducted under nitrogen using a Thermal Product Solutions (TPS) Blue M heating oven (Model No.: DCI-336-C-MP550), White Deer, Pa., U.S.A. After purging with nitrogen, the annealing temperature was initially kept at 60° C. for two hours, followed by 100° C. for an additional 6 hours. After annealing, the cooled films were stored under vacuum until further testing. Heat treatments (annealing) are advantageously conducted under an inert atmosphere to minimize unwanted hydrolysis and/or oxidation.

EXAMPLE 14

Film Formation by Melt Extrusion of the Resin of Example 3B a) Melt Extrusion

The melt film extrusion of the resin of Example 3B was conducted in a similar fashion as described in Example 13 above. For this resin, the extruder temperatures were slightly higher due to the slightly higher molecular weight resulting in a slightly higher melt viscosity of the Example 3B resin. Throughout the different barrel zones, the temperature ranged from 160° C. to 200° C., with the die temperature kept at 200° C. A screw speed of 14.0 rpm was used, while the linear speed of the pull out roll was maintained at 5.0 fpm. During film collection, a silicone release paper dispensed from a roll stand was used to separate the film layers being wound on the take-up roll. After extrusion, the film with corresponding silicone release paper was unrolled and cut to convenient lengths. The cut films were then stored under vacuum, sandwiched between silicone release paper, prior to further use. The thickness of the film was also 3.0 mil.

b) Post-Treatment—Annealing

The annealing of the films of Example 14 prepared using the resin of Example 3B of the present invention was conducted using identical conditions to those described in Example 13 above.

EXAMPLE 15

Subjective Mechanical Property Description

Both annealed films of Examples 13 and 14 were colorless, smooth, pliable, yet not tacky. Upon extensive physical treatments, including repeated bending procedures, pulling and other subjective handling operations, the films did not tear or showed any sign of damage.

EXAMPLE 16

Thermal Analysis Before and after Annealing

Differential Scanning calorimetry (DSC) measurements were conducted using a Model Q20-3290 calorimeter from TA Instruments (New Castle, Del.) equipped with an automatic sampler. In individual experiments, between 5 and 10 mg samples of the 3-mil polymer films, unannealed or heat treated (annealed), as described in Examples 13 and 14, were placed into DSC pans, quenched below −60° C., and heated at the constant heating rate of 10° C./min to determine their calorimetric properties (first heat properties); these included the glass transition temperature, $T_g$, the crystallization temperature, $T_C$, the heat of crystallization, $\Delta H_C$, the melting point, $T_m$ and the heat of fusion, $\Delta H_m$. The films were subsequently melted at 200° C. and then quenched below −60° C. to collect "Second Heat" data. From the second heat measurements values for $T_g$, $T_m$, $T_c$ (crystallization temperature), $\Delta H_C$, and $\Delta H_m$ were obtained that are independent from the samples previous heat treatment history. Data obtained using calorimetry measurements are summarized in Table 5.

TABLE 5

Thermal (Calorimetric) Properties of Unannealed and Annealed 3-mil Extruded Films

| | First heat | | | | | Second heat* | | | |
|---|---|---|---|---|---|---|---|---|---|
| Film ID | $T_g$ (° C.) | $T_C$ (° C.)/ $\Delta H_C$ (J/g) | $T_m$ (° C.) | $\Delta H_m$ (J/g) | % Cryst.** | $T_g$ (° C.) | $T_C$ (° C.)/ $\Delta H_C$ (J/g) | $T_m$ (° C.) | $\Delta H_m$ (J/g) |
| Example 13-Unanneal | 15.4 | 76.8/ 21.0 | 165.6 | 26.4 | 28% | 25.0 | 114.6/ 25.8 | 166.3 | 26.3 |
| Example 13-Annealed | −3.0 | none | 166.6 | 28.9 | 31% | 26.0 | 112.4/ 25.7 | 167.1 | 27.0 |
| Example 14-Unanneal | 45.0 | 86.0/ 24.3 | 166.5 | 27.3 | 29% | 52.5 | 117.4/ 29.0 | 167.5 | 29.5 |
| Example 14-Annealed | −30.0 | none | 167.0 | 34.0 | 36% | 53.2 | 116.3/ 30.1 | 167.7 | 30.6 |

*The second heat DSC measurements for the films of the present invention were started by melting the resin at 200° C. for 2 minutes, with a subsequent quench (−60° C./min) to −10° C., followed by the constant heating scan at 10° C./min.
**Based on the heat of fusion of 100 PLLA resin = 93.7 J/g.

Annealed films of the present invention exhibit low glass transition temperatures (below 0° C.). The exemplary films of Examples 13 and 14 exhibited levels of crystallinity of 31% and 36%, respectively, which helped enable the films to be dimensionally stable, strong, yet soft, for superb handling. It is expected that the films of the present invention will display crystallinity levels, once annealed, between about 25 percent and 40 percent.

Although this invention has been shown and described with respect to detailed embodiments thereof, it will be understood by those skilled in the art that various changes in form and detail thereof may be made without departing from the spirit and scope of the claimed invention.

We claim:

1. An absorbable foam, comprising a semi crystalline absorbable segmented copolymer, said copolymer comprising repeating units of polymerized lactide and polymerized epsilon-caprolactone, wherein the mole ratio of polymerized lactide to polymerized epsilon-caprolactone is between about 60:40 to about 75:25, said copolymer having a first heat Tg, as determined by differential scanning calorimetry at a scan rate of 10° C. per minute, equal to or less than 0° C., and a crystallinity level of about 20 percent to about 50 percent, as measured by wide angle X-ray diffraction, wherein the foam is made from a lyophilization solution having a solid content of between about 10 weight percent and 20 weight percent, and wherein the foam has a mechanical integrity at least 64 days post-implantation or having mechanical integrity after at least 64 days of incubation in a buffer of pH 7.27 at 37° C.

2. The foam of claim 1 having a thickness between about 40 mils and about 200 mils.

3. The foam of claim 1, having a crystallinity level of about 25 percent to about 50 percent.

4. The foam of claim 1, wherein the copolymer has an inherent viscosity at least about 0.5 dL/g, as measured in a 0.1 g/dl solution of HFIP at 25° C.

* * * * *